(12) United States Patent
Noda et al.

(10) Patent No.: US 11,273,284 B2
(45) Date of Patent: Mar. 15, 2022

(54) MENTAL AND PHYSICAL STATE INDUCEMENT APPARATUS, MENTAL AND PHYSICAL STATE INDUCEMENT METHOD, AND STORAGE MEDIUM STORING CONTROL PROGRAM

(71) Applicant: DENSO CORPORATION, Kariya (JP)

(72) Inventors: Saori Noda, Kariya (JP); Masaru Kakizaki, Kariya (JP); Rie Osaki, Kariya (JP)

(73) Assignee: DENSO CORPORATION, Kariya (JP)

(*) Notice: Subject to any disclaimer, the term of this patent is extended or adjusted under 35 U.S.C. 154(b) by 131 days.

(21) Appl. No.: 16/654,257

(22) Filed: Oct. 16, 2019

(65) Prior Publication Data

US 2020/0121889 A1 Apr. 23, 2020

(30) Foreign Application Priority Data

Oct. 18, 2018 (JP) .............................. JP2018-196712

(51) Int. Cl.
*A61M 21/02* (2006.01)
*A61M 21/00* (2006.01)
*B60Q 9/00* (2006.01)

(52) U.S. Cl.
CPC .............. *A61M 21/02* (2013.01); *B60Q 9/00* (2013.01); *A61M 2021/0016* (2013.01); *A61M 2021/0088* (2013.01); *A61M 2230/42* (2013.01)

(58) Field of Classification Search
CPC ............................................... A61M 21/00–02
See application file for complete search history.

(56) References Cited

U.S. PATENT DOCUMENTS

2017/0354795 A1* 12/2017 Blahnik ................ A61M 21/02

FOREIGN PATENT DOCUMENTS

| JP | 2005-237456 A | 9/2005 |
| JP | 2005-334105 A | 12/2005 |
| JP | 2010-104457 A | 5/2010 |
| JP | 2011-200438 A | 10/2011 |
| JP | 2011-200439 A | 10/2011 |
| JP | 2015-97611 A | 5/2015 |
| JP | 2015-98244 A | 5/2015 |

* cited by examiner

*Primary Examiner* — Thaddeus B Cox
(74) *Attorney, Agent, or Firm* — Maschoff Brennan

(57) ABSTRACT

A technique may be provided to determine, as a target breathing rhythm used to change a mental and physical state of a target person to a target mental and physical state, not only an exhalation period for exhaling and an inhalation period for inhaling, but also a grace period between the exhalation period and the inhalation period. The grace period is a switching period between the exhalation period and the inhalation period. The grace period is a period in which exhalation, or inhalation, or both exhalation and inhalation are enabled to be performed.

16 Claims, 8 Drawing Sheets

IN: INHALATION PERIOD
GR: GRACE PERIOD
EX: EXHALATION PERIOD

IN: INHALATION PERIOD
GR: GRACE PERIOD
EX: EXHALATION PERIOD

IN: INHALATION PERIOD
GR: GRACE PERIOD
EX: EXHALATION PERIOD

IN: INHALATION PERIOD
GR: GRACE PERIOD
EX: EXHALATION PERIOD

FIG. 9
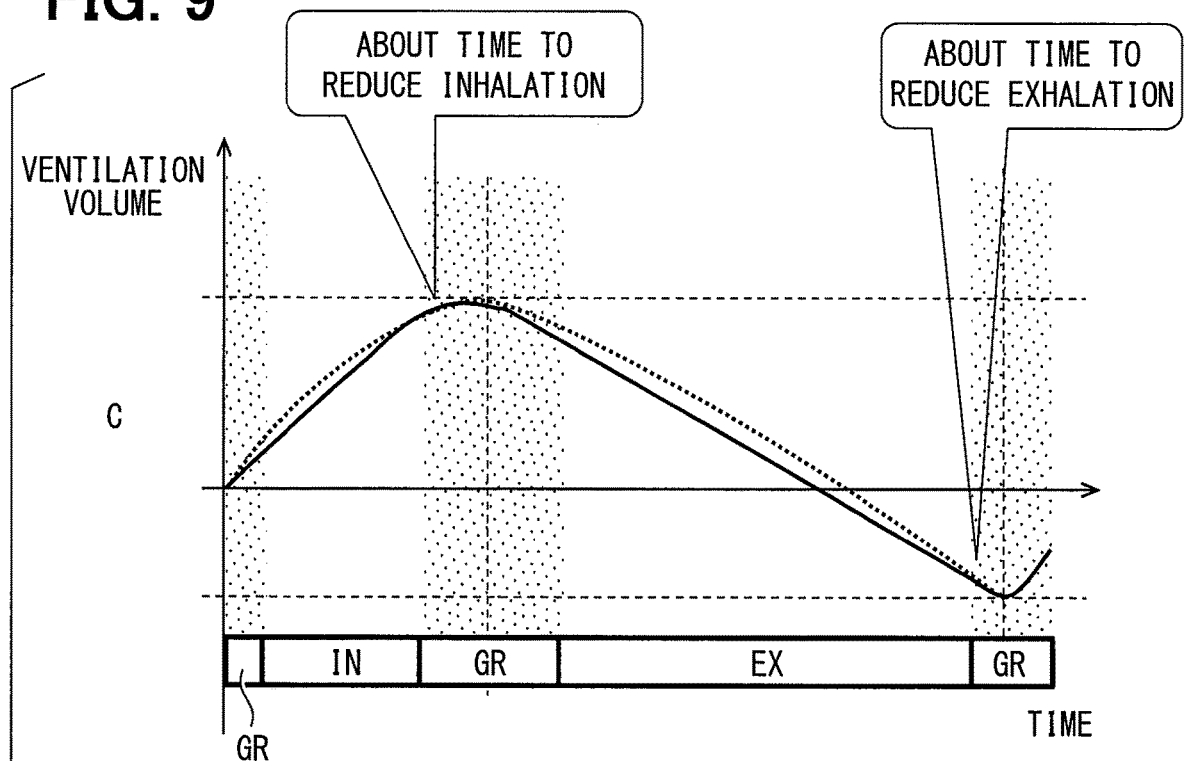
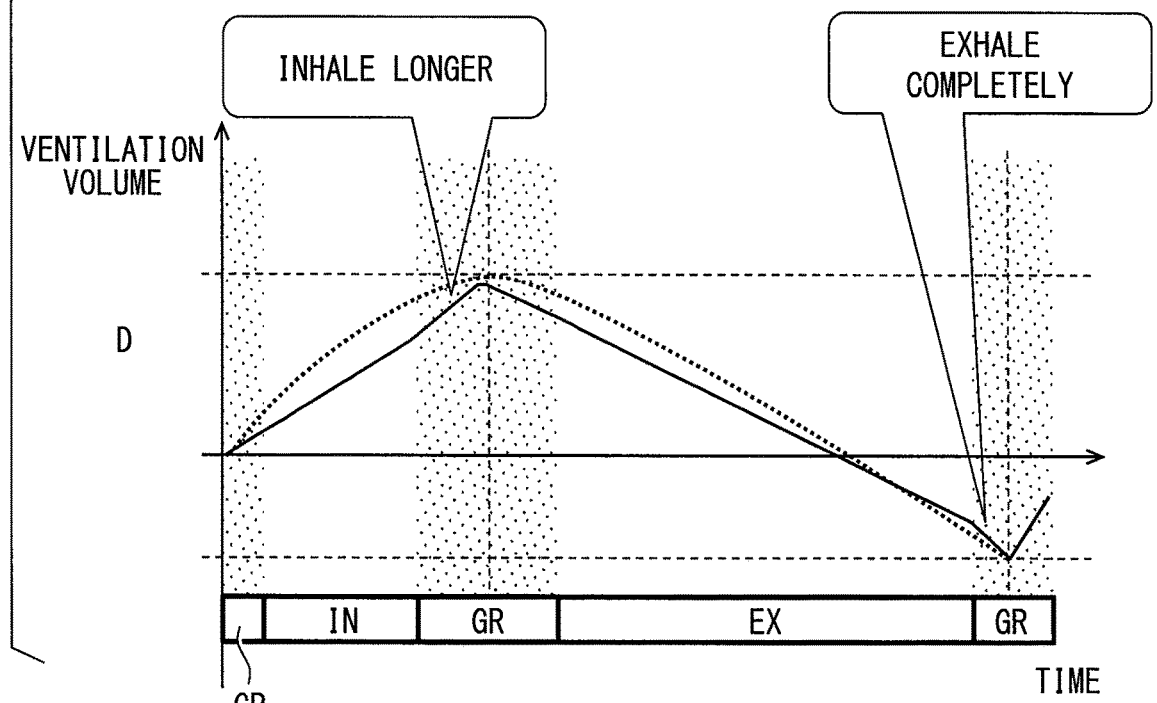
IN: INHALATION PERIOD
GR: GRACE PERIOD
EX: EXHALATION PERIOD

MENTAL AND PHYSICAL STATE INDUCEMENT APPARATUS, MENTAL AND PHYSICAL STATE INDUCEMENT METHOD, AND STORAGE MEDIUM STORING CONTROL PROGRAM

CROSS REFERENCE TO RELATED APPLICATION

The present application claims the benefit of priority from Japanese Patent Application No. 2018-196712 filed on Oct. 18, 2018. The entire disclosure of the above application is incorporated herein by reference.

TECHNICAL FIELD

The present disclosure relates to a mental and physical state inducement apparatus, a mental and physical state inducement method, and a storage medium storing a control program, which change a mental and physical state of a target person by inducing the timing of breathing of the target person.

BACKGROUND

There is a technique which suppresses anger or excitement of a target person by inducing the timing of breathing of the target person. For example, a technique is known for promoting the secretion amount of serotonin and suppressing anger and excitement by inducing a breathing exercise in a regular rhythm via display or sound to a driver.

SUMMARY

According to an embodiment of the present disclosure, a technique may be provided to determine, as a target breathing rhythm used to change a mental and physical state of a target person to a target mental and physical state, not only an exhalation period for exhaling and an inhalation period for inhaling, but also a grace period between the exhalation period and the inhalation period. The grace period is a switching period between the exhalation period and the inhalation period. The grace period is a period in which exhalation, or inhalation, or both exhalation and inhalation are enabled to be performed.

BRIEF DESCRIPTION OF DRAWINGS

The above and other objects, features and advantages of the present disclosure will become more apparent from the following detailed description made with reference to the accompanying drawings. In the drawings:

FIG. 9 is a diagram for explaining an example of effects of providing a grace period to a target breathing rhythm.

DETAILED DESCRIPTION

Figure 1:
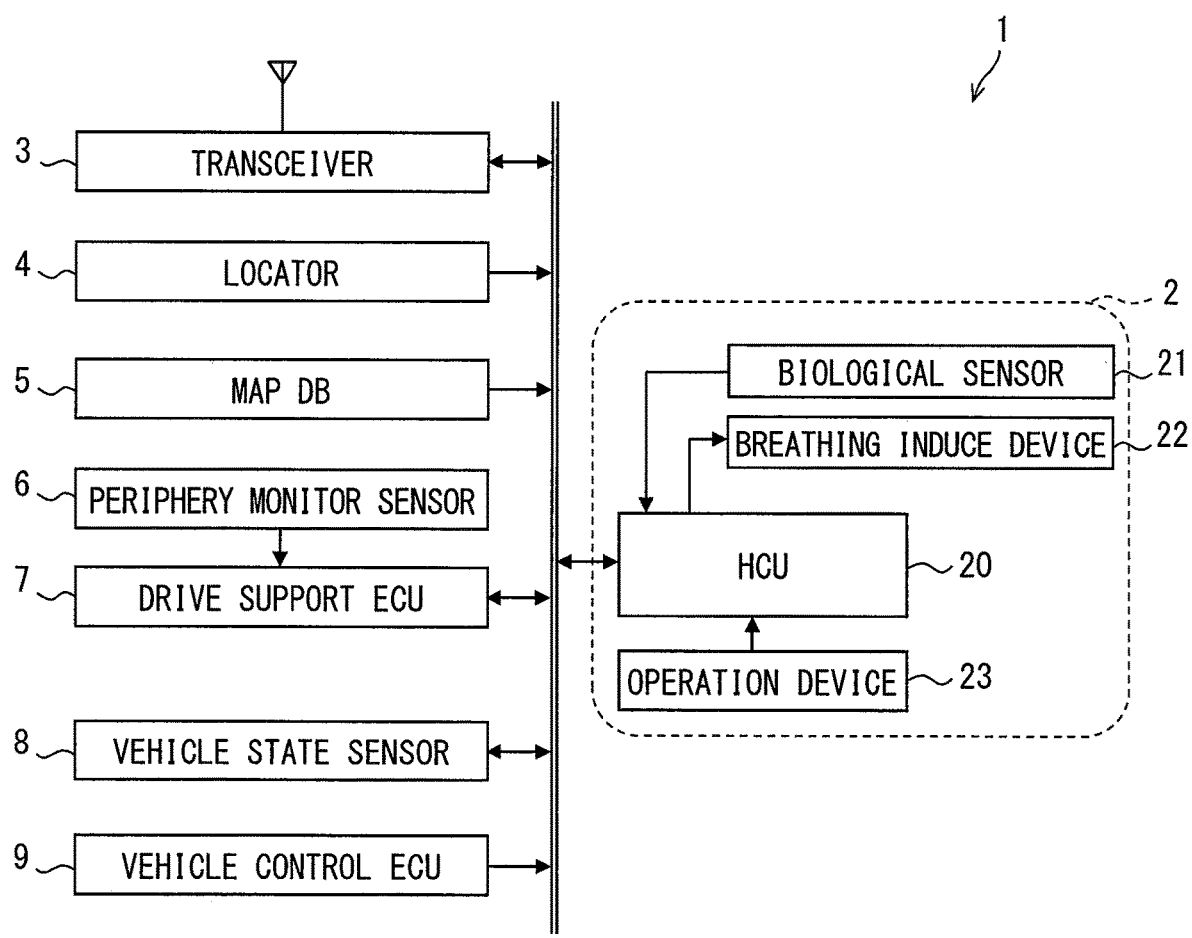
FIG. 1 is a diagram showing an example of a schematic configuration of a driving support system.

Several embodiments for the present disclosure will be described with reference to the drawings. For convenience of description, the same reference signs are assigned to portions having the same functions as those illustrated in the drawings used in the description so far among the plurality of embodiments, and a description of the same portions may be omitted. The description of other embodiments can be referred to for portions to which the same reference signs are assigned.

First Embodiment

<Schematic Configuration of Driving Support System 1>

Hereinafter, the present embodiment will be described with reference to the drawings. A driving support system 1 shown in FIG. 1 is used in a car (hereinafter simply referred to as a vehicle), and includes (i) an HMI (Human Machine Interface) system 2, a transceiver 3, a locator 4, a map database (hereinafter, map DB) 5, a periphery monitoring sensor 6, a driving support ECU (electronic control unit) 7, a vehicle state sensor 8, and a vehicle control ECU (electronic control unit) 9. The HMI system 2, the transceiver 3, the locator 4, the map DB 5, the driving support ECU 7, the vehicle state sensor 8, and the vehicle control ECU 9 are connected to, for example, an in-vehicle LAN (local area network) as an in-vehicle communication link. A vehicle on which the driving support system 1 is mounted may be hereinafter also referred to as a host vehicle.

The transceiver 3 communicates with a center or a server. The transceiver 3 may communicate with the center using a communication module for performing communication via a public communication network such as a cellular phone network or the Internet. For example, the transceiver 3 may communicate with the center via a communication network for a telematics using a vehicle communication module for telematics communication such as DCM (Data Communication Module). The transceiver 3 acquires traffic information or weather information from the center and outputs the information to the in-vehicle LAN. The transceiver 3 may communicate with the center via a roadside device.

The locator 4 includes a GNSS (Global Navigation Satellite System) receiver and an inertial sensor. The GNSS receiver receives positioning signals from several artificial satellites. The inertial sensor includes, for example, a gyro sensor and an acceleration sensor. The locator 4 sequentially measures the vehicle position of the host vehicle by combining the positioning signal received by the GNSS receiver and the measurement result of the inertial sensor. The vehicle position may be measured using a travel distance obtained from signals sequentially output from a vehicle speed sensor mounted on the host vehicle.

The map DB 5 is, for example, a non-volatile memory, and stores map data such as link data, node data, and road shapes. The link data includes data of a unique number identifying the link, a link length indicating the length of the link, link direction, link shape information, node coordinates of the start and end of the link, and road attributes. The road attributes include a road name, a road type, a road width, the number of lanes, and a speed limit value. The node data includes a various data such as a node ID in which a unique number is assigned to each node on a map, node coordinates, a node name, a node type, a connection link ID in which a link ID of a link connected to the node is described, an intersection type, and the like. Note that the map data may include a three-dimensional map including a point group of feature points of road shapes and structures. The map data may be acquired from an outside of the host vehicle using a communication module.

The periphery monitoring sensor 6 detects obstacles around the host vehicle such as pedestrians, moving objects such as other vehicles, and stationary objects such as falling objects on the road. In addition, a road marking such as lines indicating a traveling lane around the host vehicle is detected. The periphery monitoring sensor 6 includes, for example, a periphery monitoring camera for imaging a predetermined area around the host vehicle, a millimeter wave radar for transmitting a search wave to a predetermined area around the host vehicle, a sonar, or a LIDAR (Light Detection and Ranging/Laser Imaging Detection and Ranging). The periphery monitoring camera sequentially outputs a captured image to the driving support ECU 7 as sensing information. A sensor that transmits a search wave such as a sonar, millimeter wave radar, LIDAR or the like sequentially outputs a scan result based on a reception signal, which is obtained when receiving a reflection wave reflected by an obstacle, to the driving support ECU 7 as sensing information. In addition, the periphery monitoring sensor 6 may include a sensor that detects the temperature and humidity outside the host vehicle, a sensor that detects solar radiation, and the like.

The driving support ECU 7 is an electronic control unit that performs driving support for the host vehicle. The driving support ECU 7 recognizes the surrounding environment of the host vehicle from the host vehicle position of the host vehicle acquired from the locator 4, the map data acquired from the map DB 5, the sensing information acquired from the periphery monitoring sensor 6, and the like. As an example, the sensing information acquired from the periphery monitoring sensor 6 may be used to recognize the shape and movement state of an object around the host vehicle. The recognized information may be combined with the vehicle position of the host vehicle and the map data to generate a virtual space that reproduces the actual traveling environment in three dimensions. Further, the driving support ECU 7 performs driving support of the host vehicle by performing acceleration/deceleration control and/or steering control of the host vehicle in cooperation with the vehicle control ECU 9 based on the recognized surrounding environment. Examples of driving support include support for maintaining the host vehicle running in the current lane, support for moving the host vehicle at a constant speed, and support for automatically decelerating to avoid obstacles. In addition, automatic driving may be performed by causing the vehicle control ECU 9 to automatically perform acceleration, braking, and steering of the host vehicle as driving support.

The vehicle state sensor 8 is a sensor group for detecting the state of the host vehicle such as the traveling condition and the operation condition of the host vehicle. The vehicle state sensor 8 includes a vehicle speed sensor that detects the vehicle speed of the host vehicle, a steering sensor that detects the steering angle of the steering, an accelerator position sensor that detects the opening degree of the accelerator pedal of the host vehicle, and a brake stroke sensor that detects the depression amount of the brake pedal of the host vehicle. The vehicle state sensor 8 outputs the detection result to the in-vehicle LAN. The detection result from the vehicle state sensor 8 may be output to the vehicle LAN through an ECU mounted on the host vehicle. In addition, the vehicle state sensor 8 may include a sensor that detects the temperature and humidity in the passenger compartment, and a sensor that measures particulate matter such as PM 2.5 and pollen.

The vehicle control ECU 9 is an electronic control unit that performs acceleration/deceleration (i.e., speed down) control and/or steering control of the host vehicle. The vehicle control ECU 9 includes a steering ECU that performs steering control, a power unit control ECU that performs acceleration/deceleration control, a brake ECU, and the like. The vehicle control ECU 9 acquires detection signals output from sensors such as an accelerator position sensor, a brake stroke sensor, a steering angle sensor, and a vehicle speed sensor mounted on the host vehicle, and outputs control signals to the travel control devices such as an electronically controlled throttle, brake actuator, and EPS (Electric Power Steering) motor.

The HMI system 2 includes a human machine interface control unit (HCU) 20, a biological sensor 21, a breathing inducement device 22, and an operation device 23. The HMI system 2 receives an input operation from the driver, monitors the state of the driver, and presents information to the driver. The driver corresponds to a target person.

The biological sensor 21, which may be also referred to as a biometric sensor 21, measures the biological information, which may be also referred to as biometric information, of the driver, and sequentially outputs the measured biological information to the HCU 20. The biological sensor 21 may be provided on the host vehicle such as provided on a steering wheel, a driver's seat or the like, or may be provided on a wearable device worn by the driver. When the biological sensor 21 is provided in the wearable device worn by the driver, for example, the HCU 20 may obtain the measurement result of the biological sensor 21 via short distance wireless communication. Examples of biological information measured by the biological sensor 21 include breathing, pulse, heart rate and the like.

Examples of the biological sensor 21 include a pulse wave sensor such as a photoelectric pulse wave sensor that measures a heart rate or a pulse rate from a waveform of a pulse wave obtained by measurement, and an impedance type pulse wave sensor. Another example is a breathing sensor that detects the movement of breathing in a contactless manner by a Doppler sensor using Ghz band microwaves. The breathing sensor may be a pressure sensor provided on a seat back or a seat belt. In the case of estimating breathing from pulse waves, a pulse wave sensor may be used as a breathing sensor. In addition, the biological sensor 21 may be other than the ones mentioned above. Further, the biological sensor 21 may include one that measures biological information other than breathing, pulse, and heartbeat. For example, those measuring brain waves, heart rate fluctuation, sweating, body temperature, blood pressure and skin conductance can be employed.

The breathing inducement device 22 stimulates the sense of the driver to induce breathing (i.e., execute an inducement of breathing of the driver). The breathing inducement device 22 may be any one that stimulates the driver's sense of vision, smell, touch, or hearing to induce breathing, or may be a combination of these to induce breathing. The breathing inducement device 22 may induce breathing by causing the driver to recognize a target timing of breathing by the presented stimulation, or by causing the driver to breath unconsciously by the presented stimulation.

One example of the stimulation to the sense of vision is light emission from a light emitting device such as an LED. Another example of the stimulation to the sense of vision is the display of text, icons, etc. on a display device. The light emission and display may be performed at a position which the driver can visually recognize. An example of the stimulation to the sense of smell is the generation of a fragrance component from an aroma unit or the like. The fragrance component may be ejected from, for example, the front of the driver, the neck of the driver, the ceiling of the vehicle, or the like. Note that by using the aroma unit in combination with an air conditioner, the fragrance component may be ejected with the air blown from the air conditioner. One example of the stimulation to the sense of touch is wind blowing from an air conditioner. The wind blown from the air conditioner may be via an outlet directed to the driver. Other examples of the stimulation to the sense of touch include the generation of vibration by a vibrator, tightening with a seat belt, and the like. The vibrator may be provided on a member in contact with the driver, such as a steering wheel, a seat on the driver's seat, or a wearable device worn by the driver. In the case where a wearable device is provided with a vibrator, the wearable device may be configured to receive a vibration generation instruction from the HCU 20 described later via wireless communication. Examples of the stimulation to the sense of hearing include output of sound guidance from a sound output device, output of buzzer sound from a buzzer, and output of periodic environmental sound.

Examples of inducing breathing by causing the driver to recognize a target timing of breathing by the presented stimulation include light emission, display, wind blowing, vibration generation, sound guidance output, and buzzer sound output. This is because the driver can recognize the timing of breathing by the inducement if the output is display and speech. In addition, even if it is light emission, wind blowing, vibration generation, or buzzer sound output, it is possible to make the driver recognize the timing of breathing by the change of the mode of stimulation. Examples of inducing breathing by causing the driver to breathe unconsciously by the presented stimulation include generation of a fragrance component, and tightening with a seat belt. This is because the driver's deep breathing can be induced by the generation of the fragrance component among the smell component. Tightening with a seat belt can induce inhalation; loosening with a seat belt can induce exhalation.

The following will describe an example where the breathing inducement device 22 executes a basic inducement of breathing by causing the driver to recognize a target timing of breathing by light emission, and an auxiliary inducement of breathing by causing the driver to unconsciously breathe by the generation of the smell component. In this example, the breathing inducement device 22 includes a light emitting device provided on an instrument panel in front of the driver so that a light emitter of the light emitting device can change the overall color and/or brightness or the light emitter can be provided to expand and contract a bar in a bar graph-like display form to present. Further, the breathing inducement device 22 also includes a device that ejects a fragrance component (i.e., a good smell) from an instrument panel in front of the driver.

The operation device 23 is a switch group operated by the driver. For example, the operation device 23 includes a steering switch provided in a spoke portion of a steering wheel of the host vehicle, a touch switch integrated with a display device having a display, and the like. The operation device 23 corresponds to an operation input unit.

<Schematic Configuration of HCU 20>

Figure 2:
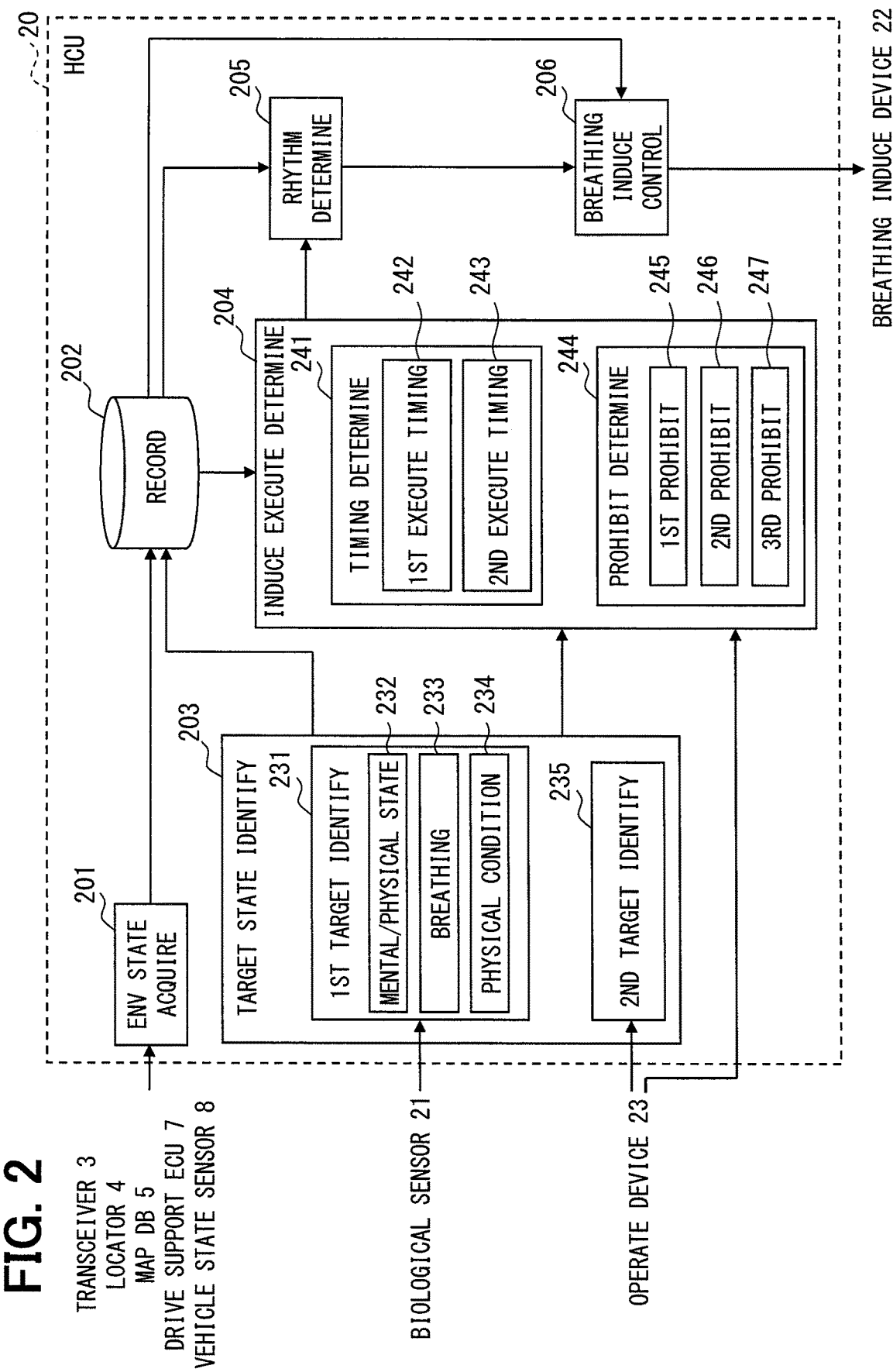
FIG. 2 is a diagram showing an example of a schematic configuration of an HCU.

The HCU 20 may correspond to a mental and physical state inducement apparatus. Subsequently, a schematic configuration of the HCU 20 will be described with reference to FIG. 2. Relating to a mental and physical state inducement related processing to be described later, the HCU 20 includes a plurality of sections (i.e., blocks) for providing respective functions, as shown in FIG. 2; the sections include an environmental state acquisition section 201, a target state identification section 203, an inducement execution determination section 204, a rhythm determination section 205, and a breathing inducement control section 206. Note that the environmental state acquisition section 201, the target state identification section 203, the inducement execution determination section 204, the rhythm determination section 205, and the breathing inducement control section 206 may be included in one or more controllers (i.e., one or more control circuits). The HCU 20 further includes a storage including an information recording storage 202. In other words, the HCU 20 may include one or more controllers and a storage. Each section may be also referred to as a module or circuit. An individual one of the above sections in the HCU 20 (i.e., one or more controllers), or an individual one of one or more controllers may be configured by including or using (i) a hardware circuit including an analog and/or digital circuit, such as one or more ICs or the like, or (ii) a central processing unit (CPU) along with a memory storing instructions executed by the CPU, or (iii) combination or both of the hardware circuit and the CPU along with the memory.

As one of examples of the present embodiment, the HCU 20 or one or more controllers may be configured to include a microcomputer having a CPU, a memory, an I/O, and a bus connecting these, and execute a control program stored in the memory to execute various processing such as a mental and physical state inducement related processing to be described later. In addition, the execution of the control program of the mental and physical state inducement related processing by the CPU corresponds to the execution of a mental and physical state inducement method corresponding to the control program. The memory referred to herein is a non-transitory computer readable tangible storage medium that stores a program and data readable by the microcomputer or a computer. In addition, the non-transitory tangible storage medium is realized by a semiconductor memory, a magnetic disk, or the like. The details of the mental and physical state inducement related processing in the HCU 20 will be described later. The present embodiment describes an example in which a target for inducement of the mental and physical state is a driver; however, there is no need to be limited thereto. A target for inducement of the mental and physical state may be an occupant of a vehicle other than the driver.

The environmental state acquisition section 201 acquires the environmental state of the host vehicle. As an example, weather information or traffic information around the vehicle position of the host vehicle received from the center by the transceiver 3 is an environmental state acquired by the transceiver 3. An example of the traffic information is the presence or absence of traffic congestion. An example of the weather information is the type of weather. Also, among the map data stored in the map DB 5, road attributes and the like in the vicinity of the vehicle position of the host vehicle to be measured by the locator 4 are environmental states acquired from the map DB 5. An example of the road attribute is a road type such as an expressway. In addition, the surrounding environment recognized by the driving support ECU 7 is acquired from the driving support ECU 7 as an environmental state. An example of the surrounding environment is the number of surrounding vehicles, the speeds of surrounding vehicles, presence or absence of retrogression, and the like. Further, the state of the host vehicle detected by the vehicle state sensor 8 is acquired from the vehicle state sensor 8 as an environmental state. One example of the state of the host vehicle is the vehicle speed, the opening degree of the accelerator pedal, the depression amount of the brake pedal, the steering angle, and the like.

The environmental state acquisition section 201 records the acquired environmental state in the information recording storage 202. The environmental state acquisition section 201 sequentially records the environmental state acquired sequentially in the information recording storage 202. The information recording storage 202 may use a non-volatile memory.

The target state identification section 203 identifies the state of the driver as a target person. The target state identification section 203 includes a first target state identification section 231 and a second target state identification section 235. The first target state identification section 231 identifies the driver's state from the result of the biological sensor 21 sensing the driver's biological information. The first target state identification section 231 includes a mental and physical state identification section 232, a breathing identification section 233, and a physical condition identification section 234.

The mental and physical state identification section 232 identifies the mental and physical state of the driver from the sensing result of the biological sensor 21. As an example, the mental and physical state identification section 232 identifies a psychological state among the mental and physical states such as "anger state", "strained state", "relaxed state", "inattentive state", "concentrated state" and the like. Note that, in this case, "anger state", "strained state", and "concentrated state" are all in a state where the tendency of activity among activity and inactivity is strong; "anger state" and "strained state" are in a state where the tendency of discomfort among comfort and discomfort is strong; "concentrated state" is in a state where in which the tendency of discomfort is weak. In addition, both "relaxed state" and "inattentive state" are in a state where the tendency of inactivity among activity and inactivity is strong; "relaxed state" is in a state where the tendency of comfort is strong; "inattentive state" is in a state where the tendency of discomfort is strong. The psychological state may be referred to, for example, Russell's Circumplex Model. In addition, the mental and physical state identification section 232 also identifies a physical state in the mental and physical state such as "sleepy state", "awake state", and the like.

The mental and physical state identification section 232 may identify the mental and physical state of the driver from the sensing result of the biological sensor 21 based on the feature quantity of the biological information for each mental and physical state. The feature quantity of the biological information for each mental and physical state may be obtained in advance by experiments and stored in the non-volatile memory of the HCU 20, or may be obtained by machine learning. The biological information used for the mental and physical state identification section 232 to identify the mental and physical state may be an image (hereinafter, face image) obtained by imaging the driver's face. In this case, the biological sensor 21 is a camera.

The breathing identification section 233 identifies the breathing of the driver from the sensing result of the biological sensor 21. The breathing identification section 233 identifies the timing of breathing of the driver from the breathing detected by the breathing sensor. That is, the period of exhalation and the period of inhalation are identified. Also, the breathing identification section 233 may identify the breathing ability such as the ventilation volume of exhalation and inhalation from the size of breathing detected by the breathing sensor. For example, suppose a case of using a pressure sensor provided on a seat belt or a seat back as a breathing sensor. In such a case, as the detection value of the pressure sensor on the seat belt becomes larger, the ventilation volume of exhalation (hereinafter, the exhalation volume) is identified larger; as the detection value of the pressure sensor on the seat back becomes larger, the ventilation volume of inhalation (hereinafter, the inhalation volume) is identified larger. The breathing identification section 233 may prompt the driver to take a deep breath by voice or display, and may identify the breathing ability during deep breathing as the driver's limit value.

The physical condition identification section 234 identifies the physical condition of the driver from the sensing result of the biological sensor 21. The physical condition identification section 234 identifies, for example, whether the driver's physical condition is abnormal. As an example, when the pulse detected by the pulse wave sensor is largely deviated from the average value of the driver, the physical condition may be identified as an abnormality unsuitable for breathing inducement. The degree of enhancement of the sympathetic nerve may be estimated from the pulse wave detected by the pulse wave sensor, and high stress may be identified as the driver's physical condition if the degree of enhancement is equal to or higher than a threshold value. Further, the physical condition identification section 234 identifies tachypnea as the physical condition of the driver when the cycle of breathing identified from the timing of breathing identified by the breathing identification section 233 is shorter than the average value of the driver by a certain amount or more. Note that each of high stress and tachypnea may be identified as an abnormality unsuitable for breathing inducement. However, in the example of the present embodiment, each of high stress and tachypnea is not identified as an abnormality unsuitable for breathing inducement.

The second target state identification section 235 identifies the driver's state from the driver's biological information or physical condition information input via the operation device 23. As an example, the second target state identification section 235 identifies a breathing ability such as vital capacity or an amount of one second based on biological information such as the driver's age, height, sex, disease, etc. input via the operation device 23. Note that the input of the vital capacity and the amount of one second may be received via the operation device 23. Further, the second target state identification section 235 identifies the driver's physical condition from the driver's physical condition information input via the operation device 23. As an example, the driver's physical condition information is selected and input from a plurality of levels such as good, normal, and poor. The target state identification section 203 sequentially records the driver's state which is sequentially identified in the information recording storage 202.

The inducement execution determination section 204 determines whether breathing inducement is executed. The inducement execution determination section 204 includes a timing determination section 241 and a prohibition determination section 244. The timing determination section 241 determines whether it is the timing to execute an inducement of breathing of the driver in the breathing inducement device 22. The prohibition determination section 244 determines whether an inducement of breathing of the driver in the breathing inducement device 22 is prohibited from being executed.

The timing determination section 241 includes a first execution timing determination section 242 and a second execution timing determination section 243. The first execution timing determination section 242 determines whether it is the timing to execute an inducement of breathing of the driver in the breathing inducement device 22 according to the driver's condition identified by the first target state identification section 231. The first execution timing determination section 242 corresponds to an execution timing determination section. The first execution timing determination section 242 determines whether it is the timing to execute an inducement of breathing of the driver in the breathing inducement device 22 according to the latest driver's state identified by the first target state identification section 231 recorded in the information recording storage 202.

The first execution timing determination section 242 determines whether it is the timing to execute an inducement of breathing of the driver in the breathing inducement device 22 in accordance with the driver's mental and physical state identified by the mental and physical state identification section 232 from the sensing result of the biological sensor 21. As an example, when the driver's mental and physical state identified by the mental and physical state identification section 232 deviates from the target mental and physical state, it is determined that it is the timing to execute an inducement of breathing. When the driver's mental and physical state identified by the mental and physical state identification section 232 corresponds to the target mental and physical state, it is the timing not to execute an inducement of breathing. More specifically, when it deviates from the target mental and physical state in the direction of activity and inactivity, it is determined that it is the timing to execute an inducement of breathing. For example, when the target mental and physical state is "concentrated state", it is determined that it is the timing to execute an inducement of breathing in the case of "inattentive state", and the timing not to execute an inducement of breathing in the case of "concentrated state". In addition, when the target mental and physical state is "relaxed state", it is determined that it is the timing to execute an inducement of breathing in the case of "anger state" or "strained state", and it is determined that it is the timing not to execute an inducement of breathing in the case of "relaxed state". In addition, when the target mental and physical state is "awake state", it is determined that it is the timing to execute an inducement of breathing in the case of "sleepy state", and it is determined that it is the timing not to execute an inducement of breathing in the case of "awake state". According to the above, when not deviating from the target mental and physical state, not executing of an inducement of breathing may be allowed.

The second execution timing determination section 243 determines whether it is the timing to execute an inducement of breathing of the driver in the breathing inducement device 22 according to the input received from the driver via the operation device 23. As an example, when an input indicating the execution of an inducement of breathing of the driver is received via the operation device 23, it is determined that it is the timing to execute an inducement of breathing. In contrast, when an input indicating stopping of an inducement of breathing of the driver is received via the operation device 23, it is determined that it is the timing to stop (that is, not execute) an inducement of breathing. This makes it possible to start and stop the inducement of breathing in the breathing inducement device 22 at the desired timing of the driver.

The prohibition determination section 244 includes a first prohibition determination section 245, a second prohibition determination section 246, and a third prohibition determination section 247. The first prohibition determination section 245 determines whether the execution of an inducement of breathing of the driver is prohibited by the breathing inducement device 22 according to the latest driver's state identified by the first target state identification section 231, which is recorded in the information recording storage 202. The first prohibition determination section 245 determines whether the execution of an inducement of breathing of the driver is prohibited in the breathing inducement device 22 according to the driver's physical condition identified by the physical condition identification section 234 from the sensing result of the biological sensor 21. As an example, when the driver's physical condition identified by the physical condition identification section 234 is an abnormality unsuitable for the above-described breathing inducement, it is determined that the execution of the breathing inducement is prohibited. According to this, when the driver's physical condition is an abnormality unsuitable for breathing inducement, it is possible to prohibit the execution of the breathing inducement.

The second prohibition determination section 246 determines whether the execution of an inducement of breathing of the driver in the breathing inducement device 22 according to the latest driver state identified by the second target state identification section 235, which is recorded in the information recording storage 202. The second prohibition determination section 246 determines whether the execution of the inducement of breathing of the driver in the breathing inducement device 22 according to the driver's physical condition identified by the second target state identification section 235 from the driver's physical condition information input via the operation device 23. As an example, when the driver's physical condition identified by the second target state identification section 235 is an abnormality unsuitable for an inducement of breathing, it is determined that the execution of an inducement of breathing is prohibited. For example, in the case where the driver's physical condition identified by the second target state identification section 235 is the above-described three levels of good, normal, and poor, for example, the physical condition being poor may be determined as an abnormality unsuitable for an inducement of breathing. According to this, when the driver's physical condition is an abnormality unsuitable for an inducement of breathing, it is possible to prohibit the execution of an inducement of breathing.

The third prohibition determination section 247 determines whether the execution of an inducement of breathing of the driver is prohibited in the breathing inducement device 22 according to the environmental state of the host vehicle acquired by the environmental state acquisition section 201 recorded in the information recording storage 202. For example, the third prohibition determination section 247 may determine that the execution of an inducement of breathing is prohibited when it is estimated that the environmental state is high in driving load. The environmental state being high in driving load includes: the host vehicle's speed being greater than a speed in a low-speed traveling such as in a traffic jam; the number of peripheral vehicles being greater than a certain value; sunlight being backlit; rainy weather; snowy weather; temperature and humidity at which road surface freezing is estimated; driving in the city; and the case where the amount of change in steering angle is large. The environmental state that is not determined to prohibit an inducement of breathing of the driver from being executed in the breathing inducement device 22 includes: congestion on expressways; and stopping at red lights. According to this, it is possible to prohibit the execution of an inducement of breathing when the driving load is high and the driver has to concentrate on the driving operation. Note that, in cases where the host vehicle is under automatic driving, the third prohibition determination section 247 may be also configured to estimate an environmental state to be high in driving load only with respect to an environmental state where the periphery monitoring sensor 6 is highly likely to fail to sense.

In addition, suppose a case where the interior in which the driver who is a target person is located is under an environmental state unsuitable for deep breathing. In such a case, the third prohibition determination section 247 determines that the execution of the inducement of breathing is prohibited. The environmental state in which the interior is unsuitable for deep breathing is a case where the temperature in the interior is higher than a predetermined value. The predetermined value here may be a high temperature which is estimated to be unsuitable for deep breathing. Other examples of environmental state unsuitable for deep breathing in the interior include a case where the concentration of particulate matter such as PM2.5 and pollen in the interior is above a predetermined value. The predetermined value here may be a high concentration which is estimated to be unsuitable for deep breathing.

The rhythm determination section 205 determines an exhalation period, an inhalation period, and a grace period as a target breathing rhythm for changing the driver's mental and physical state to a target mental and physical state. The exhalation period is a period in which the driver exhales, that is, a period in which exhalation is performed. The inhalation period is a period in which the driver inhales, that is, a period in which inhalation is performed. The grace period is a period of switching between exhalation and inhalation; in the grace period, exhalation and/or inhalation is performed. In the target breathing rhythm, a grace period is provided between the exhalation period and the inhalation period and between the inhalation period and the exhalation period. The rhythm determination section 205 executes processing in the case where it is determined by the timing determination section 241 that it is the timing to execute an inducement of breathing of the driver, and simultaneously, it is not determined that the prohibition determination section 244 prohibits the execution of an inducement of breathing of the driver in the breathing inducement device 22.

The rhythm determination section 205 determines a target breathing rhythm in accordance with a target mental and physical state. For example, when the mental and physical state identified by the mental and physical state identification section 232 is "anger state" or "strained state", the target mental and physical state may be "relaxed state". Further, when the mental and physical state identified by the mental and physical state identification section 232 is the "inattentive state", the target mental and physical state may be "concentrated state". When the mental and physical state identified by the mental and physical state identification section 232 is "sleepy state", the target mental and physical state may be "awake state".

As an example, when the target mental and physical state is "relaxed state", the parasympathetic nerves may be made dominant to induce the driver to be "relaxed state" by setting the target breathing rhythm to extend the exhalation period with respect to the inhalation period. Herein, "to extend the exhalation period with respect to the inhalation period" may signify (i) extending the exhalation period to be longer than the inhalation period or (ii) extending the exhalation period to be longer than the exhalation period (of the driver in the normal state) with respect to the inhalation period of the driver in the normal state. In addition, when the target mental and physical state is "concentrated state" under "sleepy state" being identified, the parasympathetic nerve may be suppressed to induce the driver to be "concentrated state" and "awake state" by setting the target breathing rhythm to shorten the exhalation period with respect to the inhalation period. Herein, "shortening the exhalation period with respect to the inhalation" may signify (i) shortening the exhalation period to be shorter than the inhalation period, or (ii) shortening the exhalation period to be shorter than the exhalation period (of the driver in the normal state) with respect to the inhalation period of the driver in the normal state. This can determine the target breathing rhythm that can be easily induced to the mental and physical state for each of the target mental and physical states.

Note that the exhalation period and the inhalation period in the normal state may be representative values of the exhalation period and the inhalation period identified by the breathing identification section 233 and accumulated in the information recording storage 202 under the condition that the breathing inducement of the driver is not executed by the breathing inducement device 22. The representative value may be a mode value, an average value, or a median value.

Further, it is preferable that the rhythm determination section 205 determine a target breathing rhythm according to the breathing ability of the driver. The breathing ability may be identified by the breathing identification section 233 from the sensing result of the biological sensor 21 or identified by the second target state identification section 235 from the driver's biological information input via the operation device 23. The breathing ability may be the aforementioned limit value. As the breathing ability increases, the rhythm determination section 205 may determine the lengths of the exhalation period and the inhalation period to be the values close to the ideal exhalation period and the inhalation period determined according to the target mental and physical state. As the breathing ability decreases, the rhythm determination section 205 may determine the lengths of the exhalation period and the inhalation period to be the values closer to the exhalation period and the inhalation period in the normal state of the driver from the exhalation period and the inhalation period according to the target mental and physical state. This can determine a realistic target breathing rhythm according to the breathing ability of the driver. However, even when the lengths of the exhalation period and the inhalation period are changed according to the breathing ability, it is preferable not to change the ratio of the exhalation period to the inhalation period according to the target mental and physical state. This is because it is considered that the ratio between the exhalation period and the inhalation period is highly relevant to the effect of the inducement of the mental and physical state.

Furthermore, it is preferable that the rhythm determination section 205 determine the target breathing rhythm according to the physical condition of the driver. The physical condition may be identified by the physical condition identification section 234 from the sensing result of the biological sensor 21 or identified by the second target state identification section 235 from the driver's physical condition information input through the operation device 23. According to the deterioration of the physical condition, the rhythm determination section 205 determines the lengths of the exhalation period and the inhalation period to be closer to the exhalation period and the inhalation period in the normal state of the driver from the ideal exhalation period and the inhalation period according to the target mental and physical state. This can determine a realistic breathing rhythm according to the driver's physical condition. However, even when the lengths of the exhalation period and the inhalation period are changed according to the physical condition, it is preferable not to change the ratio of the exhalation period to the inhalation period according to the target mental and physical state. This is because it is considered that the ratio between the exhalation period and the inhalation period is highly relevant to the effect of the inducement of the mental and physical state. Note that the rhythm determination section 205 does not determine the target breathing rhythm when the physical condition of the driver is determined to have an abnormality unsuitable for breathing inducement by the first prohibition determination section 245 or the second prohibition determination section 246.

The rhythm determination section 205 may determine the grace period according to the exhalation period and the inhalation period, and may shorten the grace period as the exhalation period and the inhalation period become shorter. For example, if the exhalation period is 4 seconds and the inhalation period is 8 seconds, the grace period may be set to 1 second. In contrast, if the exhalation period is 2 seconds and the inhalation period is 4 seconds, the grace period may be set to 0.5 seconds. Setting of the grace period makes the driver feel less breathless by adjusting breathing using the grace period while adjusting to the exhalation period and the inhalation period of the target breathing rhythm. The grace period is not provided by simply adding the period equivalent to the grace period to the cycle length of the exhalation period and the inhalation period in the case where the grace period is not considered. Instead, the grace period is provided by replacing a part of the exhalation period and the inhalation period by the grace period while maintaining the ratio of the exhalation period and the inhalation period in the case where the grace period is not considered.

In addition, when changing the target breathing rhythm according to the breathing ability and/or physical condition, the rhythm determination section 205 may not change the ratio of the exhalation period to the inhalation period according to the target mental and physical state, but may change the ratio of the grace period to the exhalation period and the inhalation period. More specifically, the ratio of the grace period to the exhalation period and the inhalation period may be increased in response to poor breathing ability or poor physical condition. According to this, as the breathing ability of the driver decrease and the driver thus becomes harder to match the exhalation period and the inhalation period of the target breathing rhythm, the ratio of the grace period is increased. This makes it easy to control breathing using the grace period.

As an example, the map is provided in which the breathing ability, physical condition, and the target mental and physical state are associated with the target breathing rhythm. The rhythm determination section 205 may use the map so as to determine the target breathing rhythm according to the breathing ability, physical condition, and target mental and physical state. The map may be obtained by experiments, simulations, etc. and stored in advance in the non-volatile memory of the HCU 20 so that the map may be used by the rhythm determination section 205. In addition, a target mental and physical state may include a transition state from a mental and physical state before inducement to a target mental and physical state. That is, the target mental and physical state may be paraphrased as a target movement.

The breathing inducement control section 206 controls the breathing inducement device 22 so that the driver performs breathing in accordance with the target breathing rhythm determined by the rhythm determination section 205. The breathing inducement control section 206 causes the breathing inducement device 22 to stimulate the driver's sense organ in such a mode to differentiate the exhalation period, the inhalation period, and the grace period of the target breathing rhythm determined by the rhythm determination section 205, to thereby induce the driver to breathe in accordance with the target breathing rhythm.

As one example, suppose a case where the breathing inducement device 22 stimulates the driver's sense of vision by the light emission of the light emitter. In such a case, the color of light emission is differentiated for the respective exhalation period, the inhalation period, and the grace period so that each of the exhalation period, the inhalation period, and the grace period may be distinguishable from each other. This allows the driver to recognize each of the exhalation period, the inhalation period, and the grace period. Thus, the driver is enabled to change the timing of breathing such that the driver exhales during the exhalation period, inhales during the inhalation period, and adjusts switching of breathing in the grace period. In addition, since the driver can recognize the grace period, the breathing can be adjusted using the grace period to reduce the driver's breathlessness due to the timing of switching between exhalation and inhalation not being synchronized. Note that in the grace period, the color of the exhalation period and the color of the inhalation period may be alternately illuminated to distinguish the exhalation period, the inhalation period, and the grace period from each other.

Figure 3:
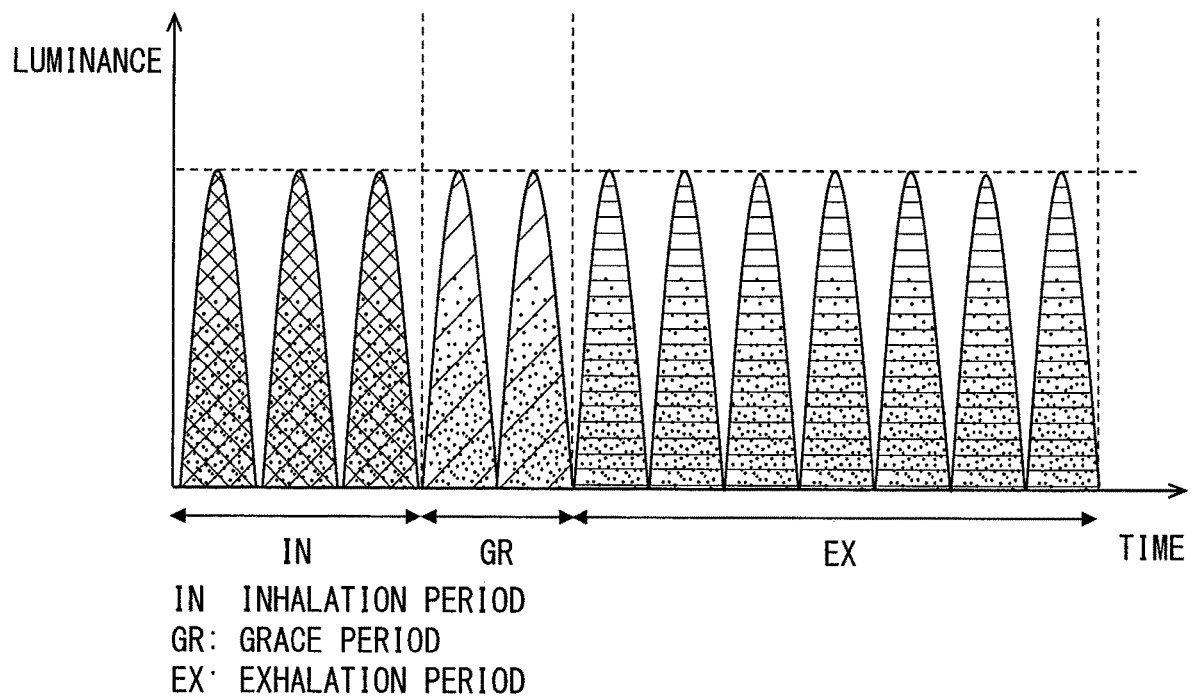
FIG. 3 is a view for explaining an example of a mode of presentation of a target breathing rhythm by light emission in a breathing inducement device.

The breathing inducement control section 206 may be configured to periodically blink the light emitting unit by periodically changing the luminance of the light emitter as shown in FIG. 3. The vertical axis of FIG. 3 indicates the luminance of the light emitter; the horizontal axis indicates the time. The solid line indicates the temporal change of the luminance. According to this, since the light emitter blinks periodically, such blinking period or cycle allows the driver to easily grasp (i) the exhalation period, the inhalation period, and the grace period, and (ii) the timing of switching of the exhalation period, the inhalation period, and the grace period. Also in the example of FIG. 3, each period can be distinguished by making the color of light emission different among the exhalation period, the inhalation period, and the grace period. The grace period may be distinguishable from the exhalation period and the inhalation period by using a color different from the colors of the exhalation period and the inhalation period. Further, the grace period may be more easily recognized by using an intermediate color between the color of the exhalation period and the color of the inhalation period.

Figure 4:
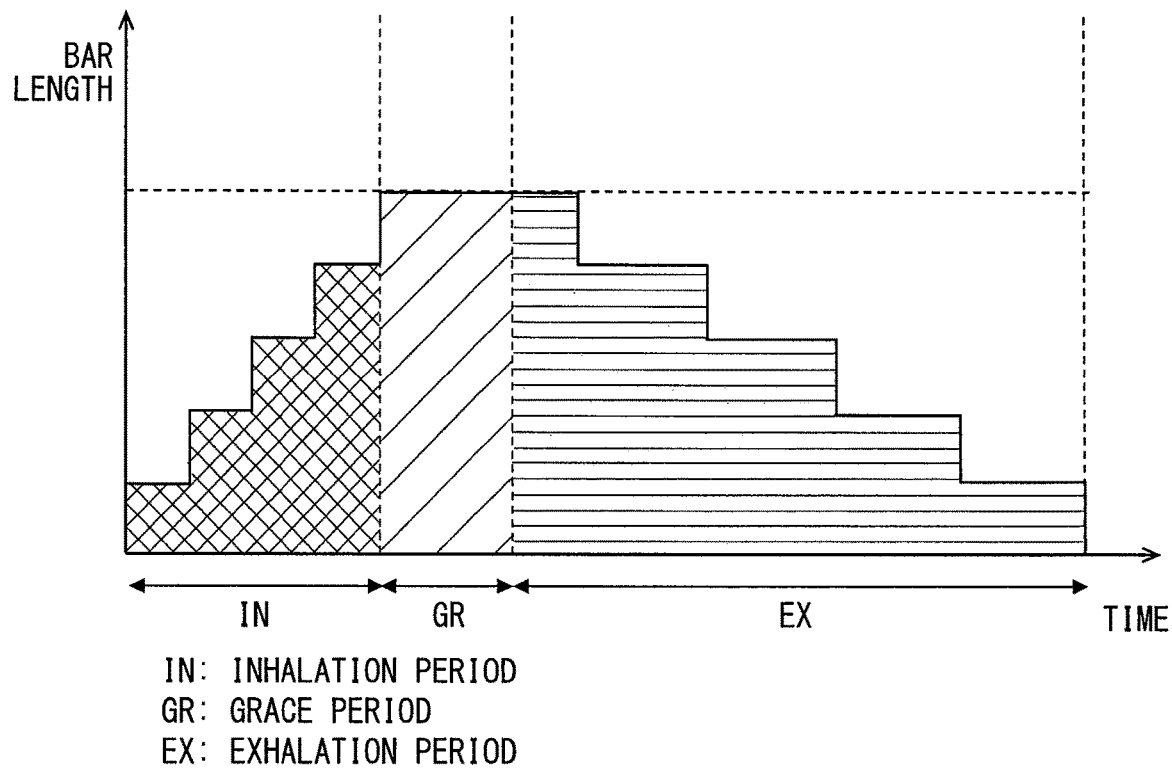
FIG. 4 is a view for explaining an example of a mode of presentation of a target breathing rhythm by light emission in a breathing inducement device.

In addition, the breathing inducement control section 206 may employ a bar in a bar graph-like display form as shown in FIG. 4. That is, the length of the bar of the light emitter can be displayed by being expanded and contracted according to the remaining time of the exhalation period and the inhalation period. The vertical axis in FIG. 4 indicates the bar length of the light emitter; the horizontal axis indicates time. In the example of FIG. 4, the bar length is extended towards the longest length as the remaining time of the exhalation period decreases; the bar length is maintained as the longest length in the grace period; and the bar length is shortened as the remaining time of the inhalation period decreases. Also in the example of FIG. 4, each period can be distinguished by making the color of the light emission different for the exhalation period, the inhalation period, and the grace period. According to this, the lengths of the exhalation period and the inhalation period and the remaining time can be easily grasped by the length of the bar of the light emitter. Note that the grace period may be distinguishable from the exhalation period and the inhalation period by not changing the length of the bar.

In addition, while the color of light emission of each of the exhalation period, the inhalation period, and the grace period may be made different from each other, the remaining time of each of the exhalation period and the inhalation period may be expressed by the luminance of the light emission.

In addition, the breathing inducement control section 206 may be configured to be able to distinguish between (i) the exhalation period and the inhalation period and (ii) the grace period by distinguishing the change in the brightness of the light emission between (i) the exhalation period and the inhalation period and (ii) the grace period. Even when this configuration is adopted, the driver can recognize the grace period by the change in the brightness of the light emission. The grace period can thus be used to adjust breathing to reduce the driver's breathlessness due to the timing of switching between exhalation and inhalation being not matched.

Figure 5:
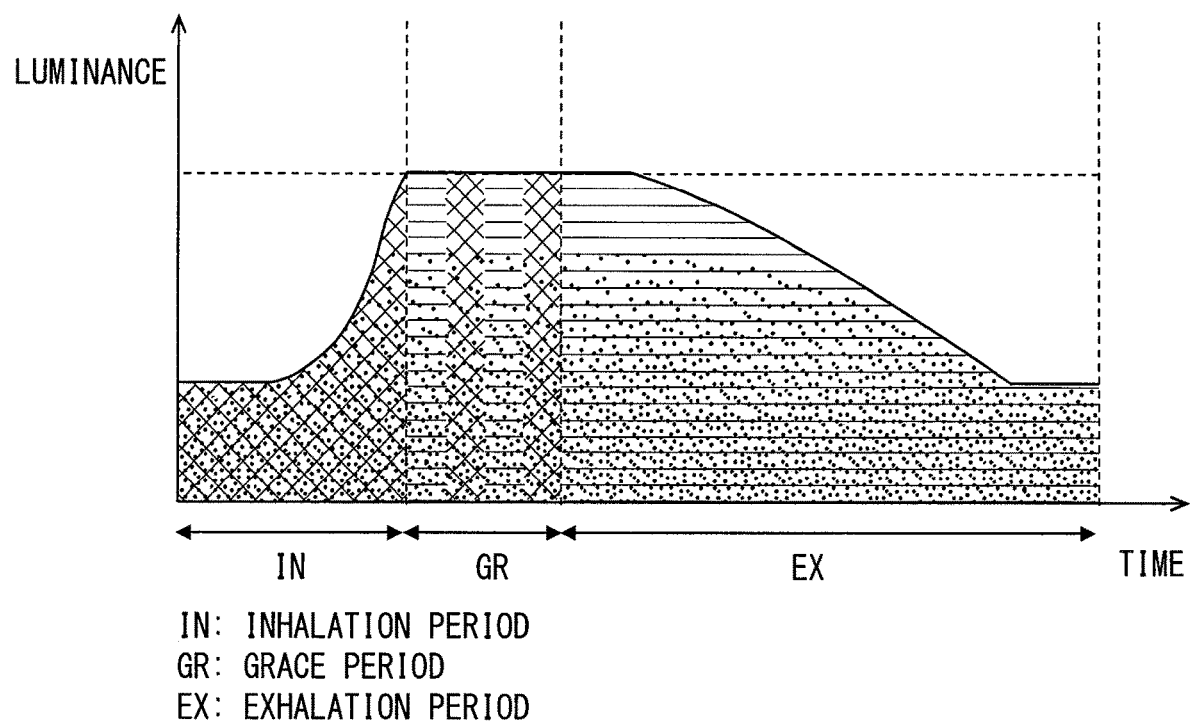
FIG. 5 is a view for explaining an example of a mode of presentation of a target breathing rhythm by light emission in a breathing inducement device.

As an example, as shown in FIG. 5, the breathing inducement control section 206 may be provided to periodically increase or decrease the luminance of the light emitter only during the grace period among the exhalation period, the inhalation period, and the grace period, thereby presenting by distinguishing the changes in the brightness of light emission between (i) the exhalation period and the inhalation period, and (ii) the grace period. As an example, as shown in FIG. 5, while the luminance may be increased as the remaining time of the inhalation period decreases, the luminance may be decreased as the remaining time of the exhalation period is decreased. The timing of the exhalation period and the inhalation period may be thus easily understood. The vertical axis in FIG. 5 indicates the luminance of the light emitter; the horizontal axis indicates time. Also in the example of FIG. 5, the exhalation period and the inhalation period can be distinguished from each other by making the color of light emission different. In addition, the breathing inducement control section 206 may be configured to change the blinking period of the light emitter only during the grace period among the exhalation period, the inhalation period, and the grace period, to thereby present by differentiating the change in the brightness of the light emission between (i) the exhalation period and the inhalation period and (ii) the grace period.

When the breathing inducement device 22 stimulates the driver's sense of touch, the breathing inducement control section 206 can distinguish the mode of stimulation by vibration or air blowing between (i) the exhalation period and the inhalation period, and (ii) the grace period. When the breathing inducement device 22 stimulates the driver's sense of hearing, the breathing inducement control section 206 can distinguish the mode of stimulation by the output of speech or the output of buzzer sound between (i) the exhalation period and the inhalation period, and (ii) the grace period. A plurality of types of stimulations may be combined such that the distinction between (i) the exhalation period and (ii) the inhalation period is performed by the color of light emission of the light emitter, while the distinction between (i) the exhalation period and the inhalation period and (ii) the grace period is performed in other than the color of light emission of the light emitter.

Also, the breathing inducement control section 206 may cause the breathing inducement device 22 to stimulate the sense organ other than the driver's sense of smell in such a manner that the exhalation period, the inhalation period, and the grace period can be distinguished from each another. In contrast, if a difference between (i) the timing of the driver's actual breathing identified by the breathing identification section 233 and (ii) the target breathing rhythm is equal to or greater than a threshold value, the breathing inducement device 22 may preferably generate a fragrance component so as to stimulate the sense of smell of the driver in the inhalation period. That is, if the timing of the driver's actual breathing identified by the breathing identification section 233 is earlier by a threshold value or greater than the target breathing rhythm, the breathing inducement device 22 may preferably generate a fragrance component so as to stimulate the sense of smell of the driver in the inhalation period.

Figure 6:
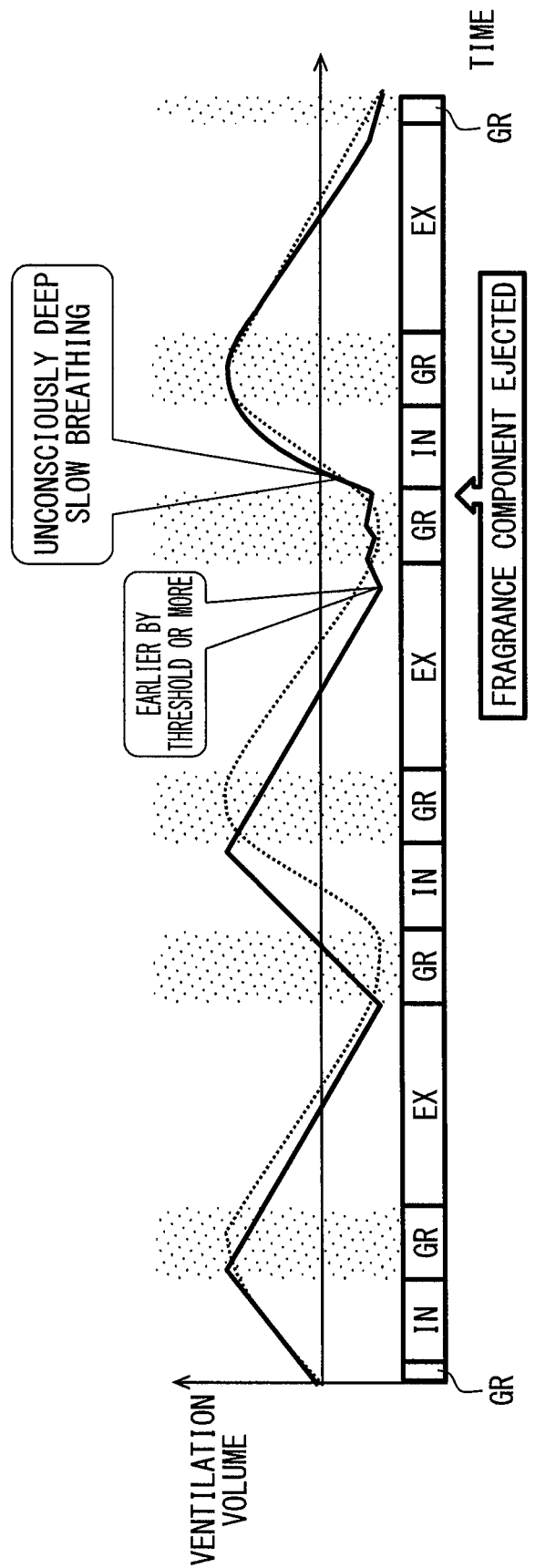
FIG. 6 is a view for explaining an example of the timing with which a breathing inducement device generates a fragrance component.

As one example, the light emission of the light emitter as described above is made to induce the driver to breathe in accordance with the target breathing rhythm. In contrast, as shown in FIG. 6, when the driver's actual exhalation period is earlier by a threshold value or more than the target breathing rhythm, the fragrance component may be preferably generated so as to stimulate the driver's sense of smell in the inhalation period. The vertical axis in FIG. 6 indicates the breathing ventilation volume; the horizontal axis indicates the time. Further, the dotted line in FIG. 6 shows the time-based change in the ventilation volume of breathing according to the target breathing rhythm, and the solid line shows the time-based change in the ventilation volume of the actual breathing of the driver. Furthermore, IN in FIG. 6 indicates an inhalation period, EX indicates an exhalation period, and GR indicates a grace period. The same applies to the subsequent FIGS. 8 and 9.

The threshold value referred to here may be a period of time that is variable appropriately. The fragrance component is a component of so-called good smell, and is a component of preferable smell for most people. In addition, the breathing inducement device 22 generates the fragrance component with a predetermined timing so as to stimulate the driver's sense of smell with the fragrance component in the inhalation period. Such a predetermined timing may be set by tracing back by a period of time from when a device ejects a fragrance component to when the fragrance component reaches a driver's nose. Therefore, the predetermined timing with which the fragrance component is generated by the breathing inducement device 22 may be in the inhalation period or the grace period. In the example of FIG. 6, the timing (i.e., a time frame or a period of time) of generating the fragrance component by the breathing inducement device 22 is in the grace period; the fragrance component generated in the grace period reaches the driver's nose in the inhalation period.

According to the above configuration, if the timing of actual breathing of the driver is earlier by a threshold value or more than the target breathing rhythm, the fragrance component is generated in the breathing inducement device 22 to stimulate the driver's sense of smell with the fragrance component in the inhalation period. The driver who has been stimulated via the sense of smell by the fragrance component is unconsciously induced to make the deep breathing. Therefore, deep and slow inhalation is performed unconsciously in the inhalation period; thus, the driver can match the target breathing rhythm without difficulty. In addition, there is no need to be limited to the case where the timing of the driver's actual breathing is earlier by a threshold value or more than the target breathing rhythm. The fragrance component may be generated by the breathing inducement device 22 so as to stimulate the driver's sense of smell with the fragrance component in the inhalation period.

In addition, a stimulation is used for the inducement of breathing in order to enhance the effect of the inducement of the mental and physical state. Such a stimulation may preferably be a stimulation that is estimated to lead to a target mental and physical state. For example, in the case where a target mental and physical state is a relaxed state, if the stimulation is light, it may be a cold color such as blue or a medium color such as green. If the stimulation is a fragrance component, a fragrance component having a relaxing effect such as cedrol may be used.

When the first execution timing determination section 242 determines that it is the timing to execute an inducement of breathing of the driver, the breathing inducement control section 206 may cause the breathing inducement device 22 to induce the breathing of the driver. In contrast, when it is determined that it is not the timing to execute an inducement of breathing of the driver, the breathing inducement device 22 may be stopped from executing an inducement of breathing of the driver. According to this, it becomes possible to start the inducement of breathing when there is deviation from the target mental and physical state, and to stop the inducement of breathing when the inducement to the target mental and physical state ends. Therefore, when it is not necessary to guide the driver to a target mental and physical state, unnecessary breathing inducement can be prevented from being executed uselessly.

When the second execution timing determination section 243 determines that it is the timing to execute an inducement of breathing of the driver, the breathing inducement control section 206 may cause the breathing inducement device 22 to execute an inducement of breathing. In contrast, when it is determined that it is not the timing to execute an inducement of breathing of the driver, it may be configured to stop the breathing inducement device 22 from executing the inducement of breathing of the driver. According to this, it is possible to start and stop the inducement of breathing at the timing desired by the driver.

If it is determined that the first prohibition determination section 245 or the second prohibition determination section 246 prohibits an inducement of breathing of the driver from being executed, the breathing inducement control section 206 prohibits the execution of the inducement even when it is the timing to execute an inducement of breathing of the driver in the breathing inducement device 22. According to this, when the driver's physical condition is an abnormality that is not suitable for breathing inducement, it is possible to prohibit the execution of breathing inducement and to prevent the physical condition from deteriorating. Even when the first prohibition determination section 245 or the second prohibition determination section 246 determines that an inducement of breathing of the driver is prohibited from being executed, it may be determined by the second execution timing determination section 243 that it is the timing to execute an inducement of breathing of the driver. In such a case, when the driver himself/herself wants, it may be configured not to prohibit the execution of the inducement of breathing.

When it is determined that the third prohibition determination section 247 prohibits an inducement of breathing of the driver from being executed, the breathing inducement control section 206 may prohibit the breathing inducement device 22 from executing an inducement of breathing of the driver even when it is the timing to execute an inducement of breathing of the driver. According to this, when the environmental state of the host vehicle is estimated to provide a high driving load, it is possible to prohibit the execution of breathing inducement and make the driver easier to concentrate on driving.

As described above, the driver can adjust his/her breathing using a grace period by providing the grace period within the target breathing rhythm and presenting the grace period in a recognizable manner to the driver. This can reduce the driver's breathlessness due to the timing of switching between exhalation and inhalation which are not synchronized. Further, a configuration may be added to further reduce the driver's breathlessness. The details are described as follows.

The breathing inducement control section 206 may be configured to monitor the breathing of the driver and/or breathing ability of the driver which is sequentially identified by the breathing identification section 233, and adjust sequentially the target breathing rhythm based on the monitored breathing and/or breathing ability.

For example, suppose a case where the driver's exhalation volume identified by the breathing identification section 233 is less than or equal to a threshold value. In such a case, even if the timing after a predetermined period of time such as one second is not the timing to start the inhalation period in the target breathing rhythm, an adjustment may be made so as to start an inhalation period in the target breathing rhythm after this predetermined period of time. The threshold value referred to here may be any value that is estimated to be weak in exhalation, and can be variable appropriately. Further, the predetermined period of time referred to here may be a period of time for which the driver is estimated to be able to wait until inhalation without feeling the breathlessness when the driver's exhalation volume is equal to or less than a threshold value. According to this, it is possible to reduce the burden on the driver and reduce the driver's breathlessness by advancing the timing to start the inhalation period when the driver's exhalation becomes weak.

In addition, suppose a case where the driver's breathing between the exhalation and the inhalation identified by the breathing identification section 233 is stopped for a period of time that is longer than a predetermined period of time. In such a case, the breathing inducement control section 206 may adjust to bring the exhalation period and the inhalation period of the target breathing rhythm closer to the exhalation period and the inhalation period of the driver in the normal state. Here, the predetermined period of time may be a period of time during which the driver is estimated to have been stopping breathing forcibly in order to match the target breathing rhythm. According to this, when the driver is forced to stop breathing in order to match the target breathing rhythm, the actual breathing rhythm is made approach the exhalation period and inhalation period of the driver in the normal state. This can reduce the burden on the driver and the breathlessness of the driver.

In addition, if the driver's exhalation period identified by the breathing identification section 233 is earlier by a threshold value or more than the exhalation period of the target breathing rhythm, the breathing inducement control section 206 may induce or urge the driver to lengthen the exhalation. The threshold value referred to here may be a period of time that is variable appropriately. In order to urge the exhalation to be lengthened, a speech such as "Let's exhale longer" may be output from a sound output device, or a display such as "Let's exhale for one second longer" may be displayed. According to this, the driver can easily adjust the timing of breathing according to the target breathing rhythm. Further, instead of urging the driver to lengthen the exhalation, the driver may be urged to intensify the inhalation. This is because it may be assumed that insufficient inhalation results in insufficient exhalation.

<Mental and Physical State Inducement Related Processing in HCU 20>

Figure 7:
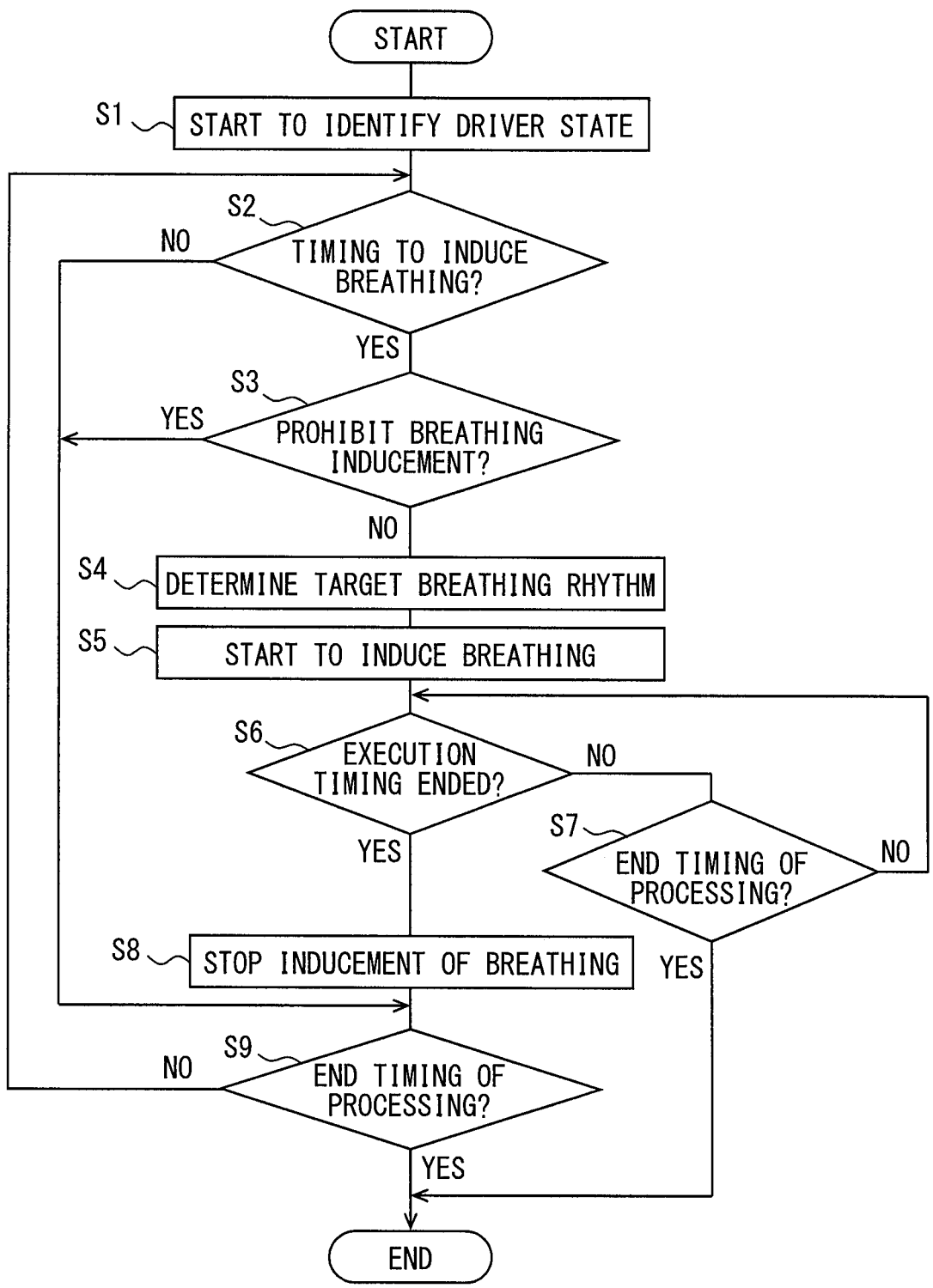
FIG. 7 is a flowchart showing an example of a sequence of mental and physical state inducement related processing in an HCU.

Subsequently, an example of the sequence of the mental and physical state inducement related processing in the HCU 20 will be described using the flowchart of FIG. 7. The flowchart of FIG. 7 may be started in response to that the power of the HCU 20 is turned on along with a switch (hereinafter referred to as a power switch) for starting an internal combustion engine or a motor generator of the host vehicle being turned on. In addition, there may be a case where the operation device 23 is used to switch on/off setting of the function for executing the mental and physical state inducement related processing. In such a case, the fact that the function for executing the mental and physical state inducement related processing is turned on may be added to the condition to start the mental and physical state inducement related processing. Note that as described above, the HCU 20 or the controller includes sections to achieve the respective functions. Such sections, which are included in the following flowchart in FIG. 7, are represented, for instance, as S1. Each of the sections may be combined with another section or be further divided into several sections. As described above, the section may also be referred to as not only a module or circuit but also as a step in the flowchart.

First, in S1, acquisition of the environmental state of the host vehicle by the environmental state acquisition section 201 and identification of the driver's state by the target state identification section 203 are started. In S2, when the timing determination section 241 determines that it is the timing to execute an inducement of breathing of the driver in the breathing inducement device 22 (YES in S2), the processing proceeds to S3. In contrast, when it is determined that it is not the timing to execute an inducement of breathing of the driver in the breathing inducement device 22 (NO in S2), the processing proceeds to S9.

In S3, when the prohibition determination section 244 determines that the execution of breathing inducement of the driver is prohibited in the breathing inducement device 22 (YES in S3), the processing proceeds to S9. In contrast, when it is not determined that an inducement of breathing of the driver in the breathing inducement device 22 is prohibited from being executed (NO in S3), the processing proceeds to S4.

In S4, the rhythm determination section 205 determines a target breathing rhythm for changing the driver's mental and physical state to the target mental and physical state. In S5, the breathing inducement control section 206 starts the breathing inducement by controlling the breathing inducement device 22 so that the driver performs breathing in accordance with the target breathing rhythm determined by the rhythm determination section 205.

In S6, when the driver's mental and physical state becomes the target mental and physical state, and the timing determination section 241 does not determine that it is the timing to execute an inducement of the driver in the breathing inducement device 22 (S6: YES), it is determined that the execution timing is ended. The processing then proceeds to S8. In contrast, in S6, when the driver's mental and physical state does not become the target mental and physical state, and the timing determination section 241 determines that it is the timing to execute an inducement of breathing of the driver in the breathing inducement device 22, it is determined that the execution timing is not ended (S6: NO). The processing then proceeds to S7.

In S7, when it is the end timing of the mental and physical state inducement related processing (YES in S7), the breathing inducement control section 206 ends the breathing inducement, and the mental and physical state inducement related processing is ended. In contrast, when it is not the end timing of the mental and physical state inducement related processing (NO in S7), the processing returns to S6 and repeats the processing. An example of the end timing of the mental and physical state inducement related processing includes a fact that the power switch of the host vehicle is turned off, and a fact that the function for executing the mental and physical state inducement related processing is turned off.

In S8, the breathing inducement control section 206 stops the inducement of breathing. In S9, when it is the end timing of the mental and physical state inducement related processing (YES in S9), the mental and physical state inducement related processing is ended. In contrast, when it is not the end timing of the mental and physical state inducement related processing (NO in S9), the processing returns to S2 and the processing is repeated.

Outline of First Embodiment

Figure 8:
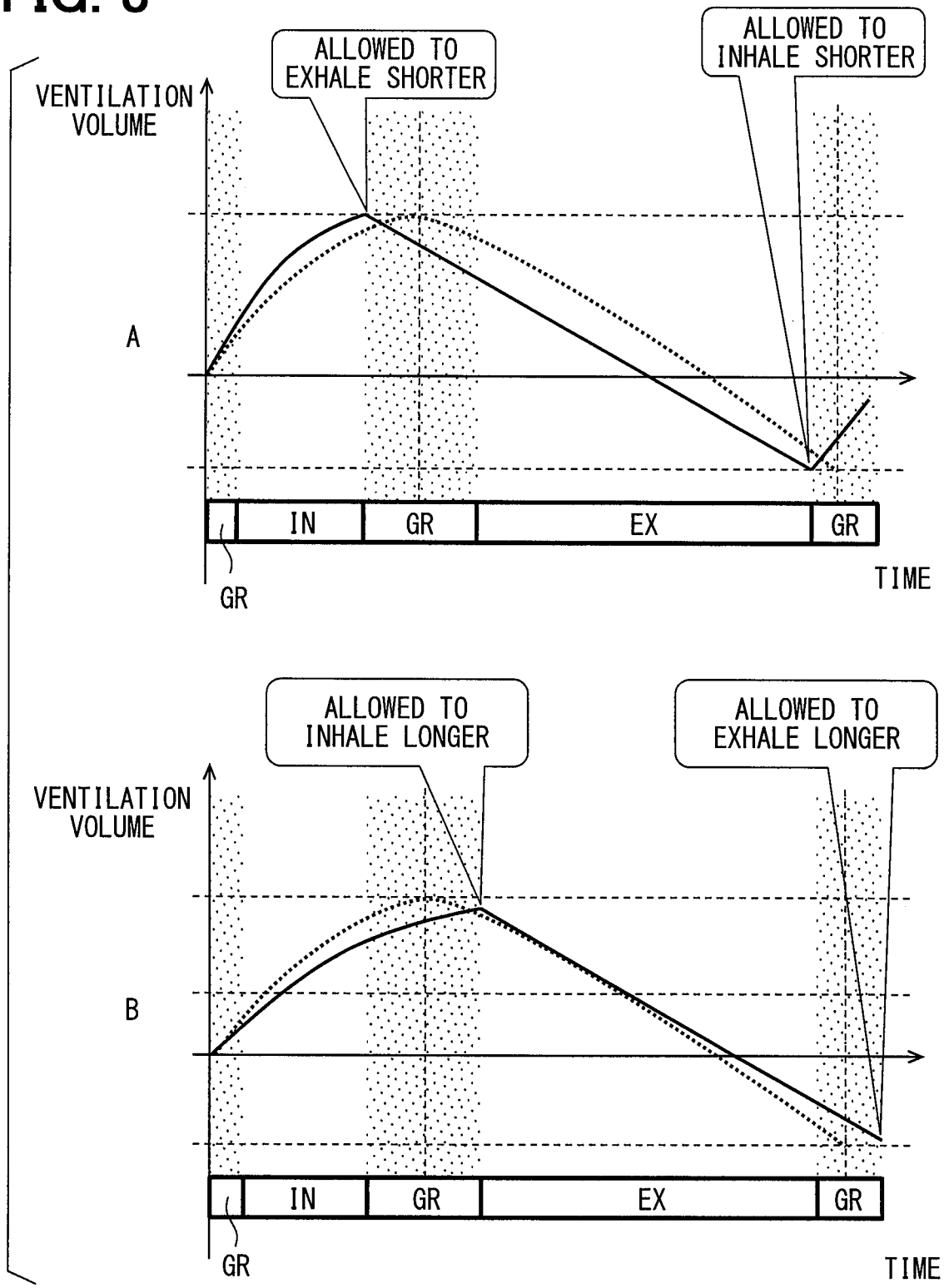
FIG. 8 is a diagram for explaining an example of effects of providing a grace period to a target breathing rhythm.

According to the configuration of the first embodiment, the target breathing rhythm for changing the driver's mental and physical state to the target mental and physical state may be provided to include a grace period in addition to an exhalation period and an inhalation period. The grace period is provided to be in between the exhalation period and the inhalation period; the grace period is a switching period in which the exhalation and/or inhalation are allowed to be performed. Therefore, as shown in FIG. 8, the timing of actual breathing can be allowed to go back and forth within the grace period. Note that A in FIG. 8 is an example in which the timing of actual breathing is allowed to be advanced, and B in FIG. 8 is an example in which the timing of actual breathing is allowed to be delayed.

Now, A of FIG. 8 illustrates a case where exhalation is desired to be earlier or shorter, or inhalation is desired to be earlier or shorter. In such a case, the grace period can be used to make exhalation earlier or shorter or make inhalation earlier or shorter while adjusting to the target breathing rhythm. Now, B of FIG. 8 illustrates a case where inhalation is desired to be later or longer, or exhalation is desired to be later or longer. In such a case, the grace period can be used to make inhalation later or longer or make exhalation later or longer while adjusting to the target breathing rhythm. This can make the driver feel less breathless while adjusting the actual breathing timing to the target breathing rhythm.

In addition, the sense organ of a target person is stimulated in a manner that can distinguish each of the exhalation period, the inhalation period, and the grace period; thus, the target person is guided or induced to breathe in accordance with the target breathing rhythm. The target person can therefor recognize the timing of the grace period in addition to the exhalation period and the inhalation period, and adjust the breathing by using the grace period. For example, as described above, while adjusting to the target breathing rhythm, it becomes possible to make the timing of actual breathing go back and forth within the grace period to make the target person feel less breathless. In addition, as shown in FIG. 9, it is also possible to switch the breathing close to the target breathing rhythm by adjusting the ventilation volume of the breathing using the grace period. Now, C of FIG. 9 illustrates a case where the change of the actual breathing ventilation volume matches the change of the ventilation volume during the exhalation period and the inhalation period of the target breathing rhythm. Now, D of FIG. 9 illustrates a case where the change in the ventilation volume of actual breathing does not match the change in the ventilation volume in the exhalation period and the inhalation period of the target breathing rhythm.

In C of FIG. 9, the change in the ventilation volume of the actual breathing matches the change in the ventilation volume in the exhalation period and the inhalation period of the target breathing rhythm. In this case, while recognizing the timing of the grace period, the driver can switch the breathing within the grace period with the same rhythm to be close to the target breathing rhythm. In D of FIG. 9, the change in the ventilation volume of the actual breathing fails to match the change in the ventilation volume in the exhalation period and the inhalation period of the target breathing rhythm. Even in this case, while recognizing the timing of the grace period, the driver can adjust the ventilation volume of the unmatched part of the breathing toward the timing of switching the breathing within the grace period so as to switch the breathing to be closer to the target breathing rhythm. For example, when the inhalation volume is insufficient, the inhalation in the grace period may be performed more strongly so as to switch breathing closer to the target breathing rhythm. In contrast, when the exhalation volume is insufficient, the exhalation in the grace period may be performed much more strongly so as to switch breathing closer to the target breathing rhythm.

Second Embodiment

The above-mentioned embodiment describes the configuration which provides a grace period to a target breathing rhythm irrespective of the target mental and physical state. There is no need to be limited thereto. For example, it may be configured to select whether to provide a grace period in the target breathing rhythm according to the target mental and physical state.

Third Embodiment

The above-mentioned embodiment describes the example which induces breathing by a fragrance component. There is no need to be limited thereto. For example, breathing may be induced by another smell component such as a pungent odor.

Fourth Embodiment

Also, another configuration may be provided such that a breathing identification section 233 may be provided to identify whether the driver is performing abdominal breathing or chest breathing. In the case where the target mental and physical state is a relaxed state, if chest breathing is performed, abdominal breathing may be proposed. Further, in the case where the target mental and physical state is a concentrated state, if abdominal breathing is performed, chest breathing may be proposed. This is because abdominal breathing is believed to make the parasympathetic nerve predominate, and chest breathing is believed to make the sympathetic nerve predominate.

Whether the driver is doing abdominal breathing or chest breathing may be detected by providing pressure sensors on the chest side and the waist side of the seat belt. The breathing identification section 233 may identify chest breathing when there is a large change in pressure on the chest side, and abdominal breathing when there is a large change in pressure on the waist side. The suggestion of chest breathing or abdominal breathing may be made by a sound output from the sound output device, or may be made by a display device.

Fifth Embodiment

The above-mentioned embodiment describes the configuration in which the HCU 20 executes the mental and physical state inducement related processing. There is no need to be limited thereto. For example, the HCU 20 and a different ECU may be configured to execute the mental and physical state inducement related processing, or a different ECU may be configured to execute the mental and physical state inducement related processing.

Sixth Embodiment

The above-mentioned embodiment describes the configuration which uses a driving support system 1 in a car. There is no need to be limited thereto. The driving support system 1 may be used in various movable bodies, and may be used in, for example, a vehicle other than a car such as a rail car or a motor bike. Further, the driving support system 1 may be used in a movable body other than a car such as an airplane and a ship. Moreover, the driving support system 1 may be used not only in a movable body but indoors other than a movable body, such as a house or a facility. In this case, the target person of the inducement of the mental and physical state in the indoors corresponds to a target person.

In addition, the control unit and the method thereof described in the present disclosure may be realized by a special-purpose or dedicated computer including a processor programmed to execute one or more functions embodied by a computer program. Alternatively, the control unit and method described in the present disclosure may be implemented by a special-purpose or dedicated hardware circuit. Alternatively, the control unit and method described in the present disclosure may be implemented by one or more dedicated computers including a combination of a processor that executes a computer program and one or more hardware circuits. The computer program may also be stored on a computer readable non-transitory tangible storage medium as computer-executable instructions. While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

For reference to further explain features of the present disclosure, the description is added as follows.

A related art describes a technique which suppresses anger or excitement of a target person by inducing the timing of breathing of the target person. For example, a technique is provided for promoting the secretion amount of serotonin and suppressing anger and excitement by inducing a breathing exercise in a regular rhythm via display or sound to the driver. Further, another technique is provided as follows. Suppose a case where the difference between the target cycle and the driver's actual cycle of the breathing exercise (hereinafter referred to as "breathing difference") is equal to or greater than a reference value, and the cycle of the breathing exercise includes an inhalation period and a subsequent exhalation period. In such a case, the start timing of the breathing cycle presented by an inducement or a guidance of breathing is matched with the start timing of the actual breathing cycle of the driver. This makes it easy to induce or guide the driver to follow the target cycle even if the driver has less intention to match the target cycle.

When inducing a target person to follow a target timing of breathing, the target person needs to perform the breathing of inhalation and exhalation according to the target timing of breathing, which may be outside a normal timing of breathing of the target person. Therefore, when the target person is induced to follow the target timing of breathing, the target person may have difficulty in breathing because the target person may not inhale or exhale sufficiently. In the technique disclosed in Patent literature 1, when the breathing difference is large and the intention of the driver to match the target cycle is small, the target timing to start the inhalation is matched to the actual start timing of the inhalation of the driver. This can reduce the breathlessness due to the timing of the inhalation not being matched (i.e., not being synchronized). However, it is not possible to reduce breathlessness due to the timing of exhalation not being synchronized. In addition, when the breathing difference is small and the intention of the driver to match the target cycle is large, the timing to start the inhalation is not matched to the actual start timing of the inhalation of the driver, either. This cannot reduce breathlessness not only due to the timing of exhalation not being synchronized but also due to the timing of inhalation not being synchronized.

It is thus desired to provide a mental and physical inducement apparatus, a mental and physical inducement method, and a storage medium storing a control program, which can reduce breathlessness of a target person due to mismatch of timing of switching between exhalation and inhalation when changing a mental and physical state of the target person by inducing the target person to follow timing of breathing.

An aspect of the present disclosure described herein is set forth in the following clauses.

According to a first aspect of the present disclosure, a mental and physical state inducement apparatus is provided to include a rhythm determination module and a breathing inducement control module. The rhythm determination module is configured to determine a target breathing rhythm used to change a mental and physical state of a target person to a target mental and physical state. The breathing inducement control module is configured to control a breathing inducement device which stimulates a sense organ of the target person to execute an inducement of breathing so that the target person breathes according to the target breathing rhythm determined by the rhythm determination module. Herein, the rhythm determination module is configured to determine the target breathing rhythm to include not only an exhalation period for exhaling and an inhalation period for inhaling, but also a grace period between the exhalation period and the inhalation period, the grace period being a switching period between the exhalation period and the inhalation period, the grace period being a period in which exhalation and/or inhalation is enabled to be performed. The breathing inducement control module is configured to induce the target person to breathe according to the target breathing rhythm by causing the breathing inducement device to stimulate the sense organ of the target person in such a manner to distinguish (i) the exhalation period, (ii) the inhalation period, and (iii) the grace period, from each other.

According to a second aspect of the present disclosure, a mental and physical state inducement method is provided as follows. The method includes determining, as a target breathing rhythm used to change a mental and physical state of a target person to a target mental and physical state, not only an exhalation period for exhaling and an inhalation period for inhaling, but also a grace period between the exhalation period and the inhalation period, the grace period being a switching period between the exhalation period and the inhalation period, the grace period being a period in which exhalation, or inhalation, or both exhalation and inhalation are enabled to be performed. The method further includes controlling a breathing inducement device to stimulate a sense organ of the target person in such a manner to distinguish (i) the exhalation period, (ii) the inhalation period, and (iii) the grace period, from each other, to induce the target person to breathe according to the determined target breathing rhythm.

According to a third aspect of the present disclosure, a non-transitory computer readable storage medium including a control program comprising computer-executable instructions stored thereupon which, when executed by a computer, cause the computer to perform as follows. The computer is caused to determine, as a target breathing rhythm used to change a mental and physical state of a target person to a target mental and physical state, not only an exhalation period for exhaling and an inhalation period for inhaling, but also a grace period between the exhalation period and the inhalation period, the grace period being a switching period between the exhalation period and the inhalation period, the grace period being a period in which exhalation, or inhalation, or both exhalation and inhalation are enabled to be performed. The computer is further caused to control a breathing inducement device to stimulate a sense organ of the target person in such a manner to distinguish (i) the exhalation period, (ii) the inhalation period, and (iii) the grace period, from each other, to induce the target person to breathe according to the determined target breathing rhythm.

According to a fourth aspect of the present disclosure, a mental and physical state inducement apparatus is provided to include one or more controllers. The one or more controllers are configured to determine, as a target breathing rhythm used to change a mental and physical state of a target person to a target mental and physical state, not only an exhalation period for exhaling and an inhalation period for inhaling, but also a grace period between the exhalation period and the inhalation period, the grace period being a switching period between the exhalation period and the inhalation period, the grace period being a period in which exhalation, or inhalation, or both exhalation and inhalation are enabled to be performed. The one or more controllers is further configured to control a breathing inducement device to stimulate a sense organ of the target person in such a manner to distinguish (i) the exhalation period, (ii) the inhalation period, and (iii) the grace period, from each other, to induce the target person to breathe according to the determined target breathing rhythm.

According to an optional aspect of the fourth aspect, an individual one of the one or more controllers may be configured by including or using (i) a hardware circuit including an analog and/or digital circuit, or (ii) a central processing unit (CPU) along with a memory storing instructions executed by the CPU, or (iii) combination or both of the hardware circuit and the CPU along with the memory.

According to the above configurations according to the first aspect, the second aspect, the third aspect, and the fourth aspect, a target breathing rhythm for changing the mental and physical state of the target person to the target mental and physical state can include not only an exhalation period for exhalation and an inhalation period for inhalation, but also a grace period between the exhalation period and inhalation period. This grace period is a switching period in which exhalation and/or inhalation may be executed. Therefore, the target person comes to feel less breathless by adjusting breathing using the grace period while matching to the exhalation period and inhalation period of the target breathing rhythm. In addition, the sense of the target person is stimulated in a manner that can distinguish the exhalation period, the inhalation period, and the grace period, from each other; thus, the target person can be induced to breathe in accordance with the target breathing rhythm. The target person can recognize the timing of the grace period in addition to the exhalation period and the inhalation period, and can use the grace period to control breathing. This leads to the reduction in breathlessness of the target person due to the mismatching of the timing of switching between the exhalation and the inhalation when changing the mental and physical state of the target person by inducing the target person to follow the target timing of breathing.

What is claimed is:

1. A mental and physical state inducement apparatus comprising:
    a rhythm determination module configured to determine a target breathing rhythm used to change a mental and physical state of a target person to a target mental and physical state; and
    a breathing inducement control module configured to control a breathing inducement device which stimulates a sense organ of the target person to execute an inducement of breathing so that the target person breathes according to the target breathing rhythm determined by the rhythm determination module,
    wherein:
    the rhythm determination module is configured to determine the target breathing rhythm to include not only an exhalation period for exhaling and an inhalation period for inhaling, but also a grace period between the exhalation period and the inhalation period, the grace period being a switching period between the exhalation period and the inhalation period, the grace period being a period in which exhalation, or inhalation, or both exhalation and inhalation are enabled to be performed; and
    the breathing inducement control module is configured to induce the target person to breathe according to the target breathing rhythm by causing the breathing inducement device to stimulate the sense organ of the target person in such a manner to distinguish (i) the exhalation period, (ii) the inhalation period, and (iii) the grace period, from each other.

2. The mental and physical state inducement apparatus according to claim 1, wherein:
    the breathing inducement device is configured to execute the inducement of breathing by stimulating at least a sense of smell of the target person by generating a fragrance component; and
    the breathing inducement control module is configured to cause the breathing inducement device to generate the fragrance component so as to stimulate the sense of smell of the target person with the fragrance component in the inhalation period, thereby inducing the target person to inhale.

3. The mental and physical state inducement apparatus according to claim 2, further comprising:
    a breathing identification module configured to identify an actual breathing timing of the target person,
    wherein:
    the breathing inducement device is capable of stimulating a sense of non-smell by other than the fragrance component to execute the inducement of breathing, in addition to stimulating at least the sense of smell of the target person by generating the fragrance component; and
    the breathing inducement control module is configured to induce the target person to breathe according to the target breathing rhythm by causing the breathing inducement device to stimulate the sense of non-smell of the target person in such a manner to distinguish (i) the exhalation period, (ii) the inhalation period, and (iii) the grace period, from each other, whereas
    in response to that a difference between the actual breathing timing of the target person identified by the breathing identification module and the target breathing rhythm identified by the rhythm determination module is equal to or greater than a threshold value, the breathing inducement control module is configured to induce the target person to inhale by causing the breathing inducement device to generate the fragrance component so as to stimulate the sense of smell of the target person with the fragrance component in the inhalation period.

4. The mental and physical state inducement apparatus according to claim 1, further comprising:
    a target state identification module configured to identify a state of the target person from a result of sensing biological information of the target person; and
    an execution timing determination module configured to determine whether it is a timing to execute the inducement of breathing of the target person by the breathing inducement device according to the state of the target person identified by the target state identification module,
    wherein
    the breathing inducement control module is configured to cause the breathing inducement device to execute the inducement of breathing of the target person in response to that the execution timing determination module determines that it is the timing to execute the inducement of breathing of the target person, whereas
    the breathing inducement control module is configured to stop the breathing inducement device from inducing the target person to breathe in response to that the execution timing determination module determines that it is not the timing to execute the inducement of breathing of the target person.

5. The mental and physical state inducement apparatus according to claim 1, further comprising:
a target state identification module configured to identify a state of the target person from a result of sensing biological information of the target person; and
a prohibition determination module configured to determine whether the breathing inducement device is prohibited from executing the inducement of breathing of the target person according to the state of the target person identified by the target state identification module,
wherein
in response to that the prohibition determination module determines that the breathing inducement device is prohibited from executing the inducement of breathing of the target person, the breathing inducement control module is configured to prohibit the breathing inducement device from executing the inducement of breathing of the target person even when it is a timing to execute the inducement of breathing of the target person.

6. The mental and physical state inducement apparatus according to claim 1, further comprising:
a target state identification module configured to identify a state of the target person from physical condition information or biological information of the target person inputted through an operation input unit; and
a prohibition determination module configured to determine whether the breathing inducement device is prohibited from executing the inducement of breathing of the target person according to the state of the target person identified by the target state identification module,
wherein
in response to that the prohibition determination module determines that the breathing inducement device is prohibited from executing the inducement of breathing of the target person, the breathing inducement control module is configured to prohibit the breathing inducement device from executing the inducement of breathing of the target person even when it is a timing to execute the inducement of breathing of the target person.

7. The mental and physical state inducement apparatus according to claim 1, further comprising:
an environmental state acquisition module; and
a prohibition determination module,
wherein:
the mental and physical state inducement apparatus is used in a movable body;
the environmental state acquisition module is configured to acquire an environmental state of an interior of the movable body and an environmental state of an exterior of the movable body;
the prohibition determination module is configured to determine whether the breathing inducement device is prohibited from executing the inducement of breathing of the target person according to the environmental state of the interior of the movable body and the environmental state of the exterior of the movable body; and
in response to that the prohibition determination module determines that the breathing inducement device is prohibited from executing the inducement of breathing of the target person, the breathing inducement control module is configured to prohibit the breathing inducement device from executing the inducement of breathing of the target person even when it is a timing to execute the inducement of breathing of the target person.

8. The mental and physical state inducement apparatus according to claim 1, wherein
in response to receiving an input providing an instruction of executing the inducement of breathing of the target person via an operation input unit, the breathing inducement control module is configured to execute the inducement of breathing of the target person by the breathing inducement device, whereas
in response to receiving an input providing an instruction of stopping the inducement of breathing of the target person via the operation input unit, the breathing inducement control module is configured to stop the inducement of breathing of the target person by the breathing inducement device.

9. The mental and physical state inducement apparatus according to claim 1, further comprising:
a target state identification module configured to identify a state of the target person from a result of sensing biological information of the target person, the target state identification module identifying at least a physical condition of the target person as the state of the target person,
wherein
the rhythm determination module is configured to change the target breathing rhythm without changing a ratio between the exhalation period and the inhalation period according to the physical condition of the target person identified by the target state identification module.

10. The mental and physical state inducement apparatus according to claim 1, wherein
the rhythm determination module is configured to change a ratio between the exhalation period and the inhalation period according to the target mental and physical state.

11. The mental and physical state inducement apparatus according to claim 1, wherein:
the breathing inducement device is configured to stimulate a sense of vision of the target person to execute the inducement of breathing of the target person by at least a light emission; and
the breathing inducement control module is configured to cause the breathing inducement device to present the exhalation period, the inhalation period, and the grace period by differentiating, in a color of the light emission, the grace period from the exhalation period and the inhalation period, enabling distinguishing of the grace period from the exhalation period and the inhalation period, to induce the target person to breathe according to the target breathing rhythm.

12. The mental and physical state inducement apparatus according to claim 1, wherein:
the breathing inducement device is configured to stimulate a sense of vision of the target person to execute the inducement of breathing of the target person by at least a light emission; and
the breathing inducement control module is configured to cause the breathing inducement device to present the exhalation period, the inhalation period, and the grace period by differentiating, in a change in brightness of the light emission, the grace period from the exhalation period and the inhalation period, enabling distinguishing of the grace period from the exhalation period and the inhalation period, to induce the target person to breathe according to the target breathing rhythm.

13. The mental and physical state inducement apparatus according to claim 1, further comprising:
one or more controllers configured to implement the rhythm determination module and the breathing inducement control module.

14. A mental and physical state inducement method comprising:
determining, as a target breathing rhythm used to change a mental and physical state of a target person to a target mental and physical state, not only an exhalation period for exhaling and an inhalation period for inhaling, but also a grace period between the exhalation period and the inhalation period, the grace period being a switching period between the exhalation period and the inhalation period, the grace period being a period in which exhalation, or inhalation, or both exhalation and inhalation are enabled to be performed; and
controlling a breathing inducement device to stimulate a sense organ of the target person in such a manner to distinguish (i) the exhalation period, (ii) the inhalation period, and (iii) the grace period, from each other, to induce the target person to breathe according to the determined target breathing rhythm.

15. A non-transitory computer readable storage medium storing a control program comprising computer-executable instructions stored thereupon which, when executed by a computer, cause the computer to perform the mental and physical state inducement method according to claim 14.

16. A mental and physical state inducement apparatus comprising:
one or more controllers configured to:
determine, as a target breathing rhythm used to change a mental and physical state of a target person to a target mental and physical state, not only an exhalation period for exhaling and an inhalation period for inhaling, but also a grace period between the exhalation period and the inhalation period, the grace period being a switching period between the exhalation period and the inhalation period, the grace period being a period in which exhalation, or inhalation, or both exhalation and inhalation are enabled to be performed; and
control a breathing inducement device to stimulate a sense organ of the target person in such a manner to distinguish (i) the exhalation period, (ii) the inhalation period, and (iii) the grace period, from each other, to induce the target person to breathe according to the determined target breathing rhythm.

* * * * *